(12) United States Patent
Ho

(10) Patent No.: US 11,071,657 B2
(45) Date of Patent: Jul. 27, 2021

(54) SYSTEM AND APPARATUS FOR A SMART DIAPER

(71) Applicant: AuSense Technologies, LLC, Austin, TX (US)

(72) Inventor: Lam Trong Ho, Austin, TX (US)

(73) Assignee: AuSense Technologies, LLC, Austin, TX (US)

( * ) Notice: Subject to any disclaimer, the term of this patent is extended or adjusted under 35 U.S.C. 154(b) by 528 days.

(21) Appl. No.: 15/594,262

(22) Filed: May 12, 2017

(65) Prior Publication Data

US 2018/0325743 A1 Nov. 15, 2018

(51) Int. Cl.
| | |
|---|---|
| *A61F 13/42* | (2006.01) |
| *A61B 5/01* | (2006.01) |
| *A61B 5/20* | (2006.01) |
| *A61B 5/00* | (2006.01) |
| *A61B 5/145* | (2006.01) |
| *A61B 5/11* | (2006.01) |

(52) U.S. Cl.
CPC ............... *A61F 13/42* (2013.01); *A61B 5/01* (2013.01); *A61B 5/14546* (2013.01); *A61B 5/208* (2013.01); *A61B 5/6808* (2013.01); *A61B 5/1113* (2013.01); *A61B 5/14532* (2013.01); *A61F 2013/421* (2013.01); *A61F 2013/424* (2013.01)

(58) Field of Classification Search
CPC ............... A61F 13/42; A61F 2013/424; A61F 2013/421; A61B 5/6808
See application file for complete search history.

(56) References Cited

U.S. PATENT DOCUMENTS

| | | | |
|---|---|---|---|
| 10,130,524 B1* | 11/2018 | Lai | A61F 13/42 |
| 2004/0078014 A1* | 4/2004 | Shapira | A61F 13/84 |
| | | | 604/361 |
| 2008/0058744 A1* | 3/2008 | Tippey | A61F 13/42 |
| | | | 604/361 |
| 2009/0005748 A1* | 1/2009 | Ales | A61F 13/42 |
| | | | 604/361 |
| 2010/0030167 A1* | 2/2010 | Thirstrup | A61F 5/445 |
| | | | 604/318 |
| 2012/0197224 A1* | 8/2012 | Chagger | A61B 5/202 |
| | | | 604/361 |
| 2013/0165809 A1* | 6/2013 | Abir | A61B 5/1135 |
| | | | 600/534 |

(Continued)

*Primary Examiner* — Susan S Su
(74) *Attorney, Agent, or Firm* — Lee & Hayes, P.C.

(57) ABSTRACT

An apparatus and a system for a smart diaper are described. These smart diapers include a disposable detection component and a reusable component including various processing circuitries. The disposable component can include a paper printed sensor pad. Paper printed sensor pads can provide for a wide detection area, and accurate determination of whether human waste is present in the diaper. Additionally, the sensor pad can determine the amount of waste exposed to the sensor pad. In certain embodiments, the sensor can also detect a temperature within the diaper. In some embodiments, the smart diapers can provide for location tracking of the wearer of the diaper, and provide notifications to the caretaker based on the location of the wearer. In some embodiments, the reusable component can be a small circular component which is mounted on the outside of the smart diapers.

19 Claims, 21 Drawing Sheets

(56) References Cited

U.S. PATENT DOCUMENTS

| | | | |
|---|---|---|---|
| 2014/0266736 A1* | 9/2014 | Cretu-Petra | A61F 13/42 340/573.5 |
| 2014/0296808 A1* | 10/2014 | Curran | G01N 27/225 604/361 |
| 2014/0350502 A1* | 11/2014 | Berland | A61F 13/42 604/361 |
| 2014/0371702 A1* | 12/2014 | Bosaeus | A61F 13/42 604/385.01 |
| 2015/0042489 A1* | 2/2015 | LaVon | H04W 52/22 340/870.11 |
| 2016/0166438 A1* | 6/2016 | Rovaniemi | A61F 13/00059 600/301 |
| 2016/0250081 A1* | 9/2016 | Pugh | G08B 21/182 604/361 |
| 2016/0314263 A1* | 10/2016 | Berland | A61F 13/42 |
| 2016/0374867 A1* | 12/2016 | Zand | A61F 13/42 604/361 |
| 2017/0156594 A1* | 6/2017 | Stivoric | A61B 5/7275 |
| 2018/0353355 A1* | 12/2018 | Carney | A61F 13/84 |
| 2019/0231608 A1* | 8/2019 | Li | A61F 13/42 |
| 2019/0287678 A1* | 9/2019 | Stevens | G16H 40/67 |

\* cited by examiner

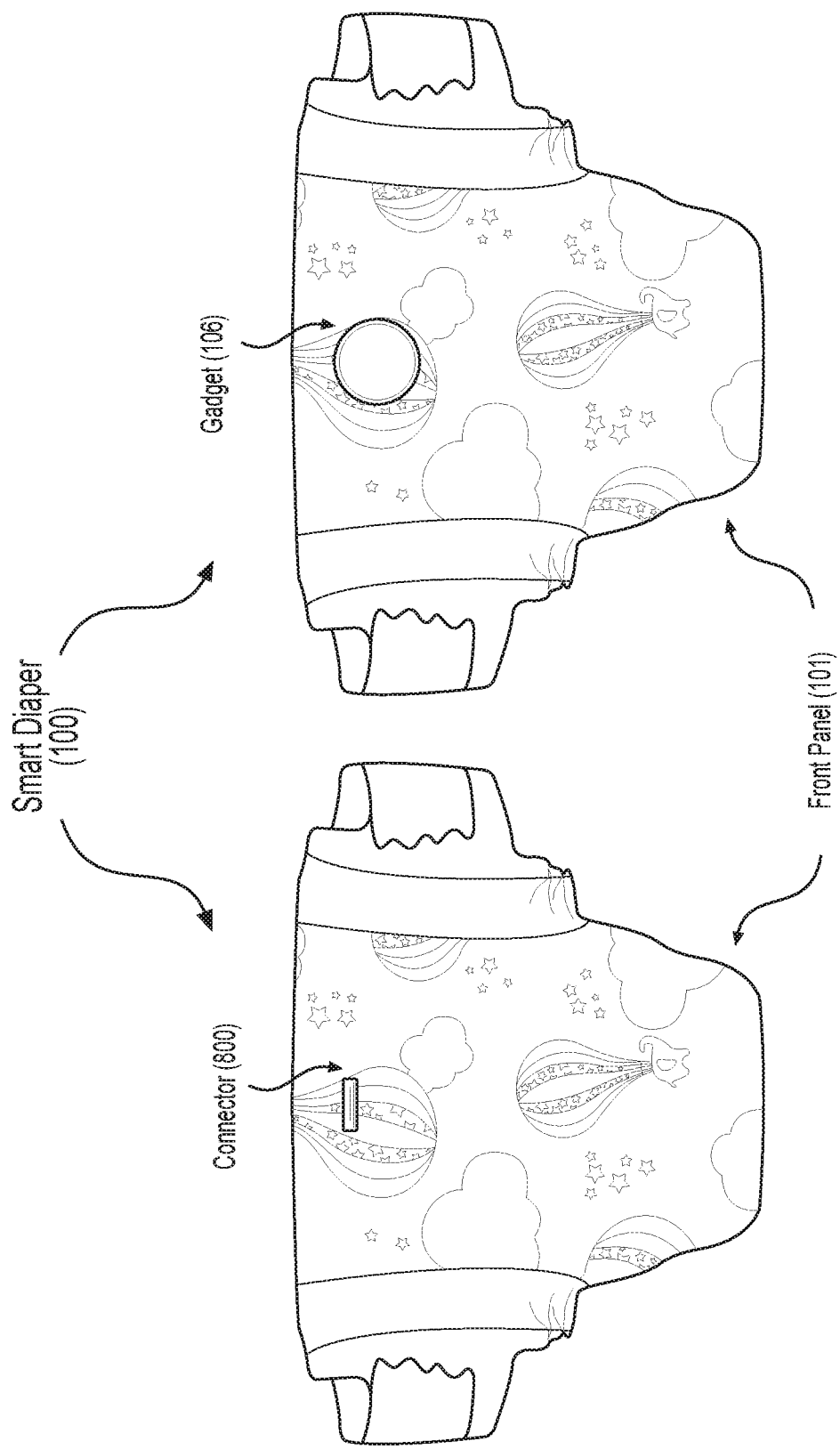

SYSTEM AND APPARATUS FOR A SMART DIAPER

BACKGROUND

Diapers or nappies are popular hygienic products. Babies, bedridden individuals, and even adults can use diapers. However, despite many advances in diaper technology, the problem of diaper rash persists. Diaper rash can be caused by the acid in urine and bowel movements of the wearer of a diaper. Although diapers today are highly absorbent and can effectively remove excess moisture from the skin, it is still recommended to change diapers as soon as the diapers are exposed to human waste. This is to prevent urine or feces from staying in contact with skin for too long. In practice, however, the determination of whether human waste is present in a diaper is very intrusive and inconvenient.

While it is possible for a caretaker to frequently check on whether human waste is present in the diaper, human waste is expelled at random times, and thus, despite the frequent checks, the skin of a diaper wearer can be exposed to human waste for a long period of time. In addition, in certain care facilities, a caretaker can be responsible for multiple patients, which would make it challenging to continuously check on each patient's diaper. Therefore, it can be beneficial to provide diapers which can notify a caretaker if human waste is present.

SUMMARY

Various solutions have been proposed concerning the notification of a caretaker when a diaper should be changed. For example, some diapers include an indicator on an outer surface of the diaper. The indicator is connected to a small detection area within the absorbent core of the diaper. The indicator changes color (or displays a sign) if exposed to human waste, thereby providing a visual clue for a caretaker that the diaper should be changed. These diapers, however, do not alert the caretaker, and the determination of whether the diaper needs to be changed requires visual inspection of the diaper. This visual inspection can be a difficult task if the caretaker is responsible for multiple individuals wearing the diapers. Moreover, because the detection area is small relative to the absorbent core, the diaper's detection can often be inaccurate.

Other diapers provide for electrical detection mechanisms. For example, some diapers provide for a stand-alone detection device. The detection device would be placed inside the diaper and once the detection device is exposed to human waste, the device would alert the caretaker. These devices tend to be bulky, and as a result, can be very inconvenient for a diaper wearer to include in the diaper. Additionally, these devices can detect only one spot within the diaper. Because of the small detection area, and because these devices can be misplaced or displaced within the diaper, the detection of these devices can be very inaccurate. Moreover, because of the cost, one would not be able to use the device as a disposable device. Therefore, each time the diaper is changed, the device has to be washed and disinfected, which can create more work for the caretaker.

Other diaper sensors include exposed wires within the diaper. These wires can be imbedded in the absorbent core of the diaper or can be placed manually by the caretaker. Properly positioning the wires within a diaper is a difficult and an expensive task. If not properly positioned in the diaper, the wires can move around and provide inaccurate detections, e.g., when short circuited. Moreover, if touched by skin, these wires can cause irritation of the skin. Additionally, reusing the wires is impractical because washing and disinfecting the wires would be difficult and time consuming. Therefore, one has to dispose of the wires after usage, and the disposable nature of these sensors adds to the per-unit cost of the diaper.

Yet other diapers include a printed circuit board. Printed circuit boards are rigid and inflexible, thereby compromising the wearer's convenience, and because of cost constraints, making the circuit boards flexible is not feasible. Since reusing the circuit boards is not a practical option (i.e., the hassle of washing and disinfecting the boards would undermine the feasibility of this option), these circuit boards are used in a disposable manner. As such, each circuit board has to be paired with a wireless device. However, this means that each new diaper will have to be paired with the wireless device prior to usage, which would mean additional work for the caretaker. Furthermore, printed circuit boards cannot cover a wide area of the diaper, thereby making the reading inaccurate.

Therefore, it is an objective of these disclosures to provide for a system and apparatus for smart diapers which would overcome some or all of these shortcomings. These smart diapers include a disposable detection component and a reusable component including various processing circuitries. As a result, the cost per unit of each diaper can be reduced drastically. In some embodiments, the disposable component can include a paper printed sensor pad. Paper printed sensor pads can provide for a wide detection area, and accurate determination of whether human waste is present in the diaper. Yet, the wearer of the diaper would not notice the presence of the sensor pad, thereby enhancing the comfort level of the wearer of the diaper. Moreover, because of the ease in production and cost-effectiveness of the components of such sensor pads, each sensor pad can be disposed of after use, and this would not increase the per-unit cost of the diapers.

Additionally, the sensor pad can determine the amount of waste exposed to the sensor pad and provide for a determination of the chemical composition of the waste. For example, by determining the conductivity of the urine exposed to the sensor pad, urine osmolality, sodium, acidity, and uncharged glucose can be measured in the urine. In certain embodiments, the sensor can also detect a temperature within the diaper. In some embodiments, the smart diapers can provide for location tracking of the wearer of the diaper, and provide notifications to the caretaker based on the location of the wearer.

In some embodiments, the reusable component can be a small circular component which is mounted on the outside of the smart diapers. In these embodiments, since the component does not directly touch the wearer's skin, the wearer's comfort can be enhanced. The reusable components tend to be the more expensive component of the smart diapers. However, because these components do not actually touch the human waste, reusing the component is sanitary, simple and cost-effective. Moreover, the component would need to be paired only once. Thus, reusing the component would obviate the need for pairing a new component each time the diapers are changed, and therefore, the caretaker's workload can be reduced.

The smart diapers of these disclosures take advantage of the principles of electrical conductivity. Specifically, certain liquids, including human urine, are capable of conducting an electric current. If a circuit line, which is disconnected between two points, is exposed to a conductive liquid covering a continuous line between the disconnected points, the circuit line would be able to conduct an electric current. In this regard, if various disconnected circuit lines are provided in a diaper, when human waste is present, the moisture and liquids present in human waste can connect the disconnected circuit lines, thereby indicating that the diaper needs to be changed.

BRIEF DESCRIPTION OF THE DRAWINGS

FIG. 11A illustrates an example smart diaper before mounting a gadget.

FIG. 11B illustrates an example smart diaper on the front panel of which a gadget is mounted.

DETAILED DESCRIPTION

The Diaper

Figure 1:
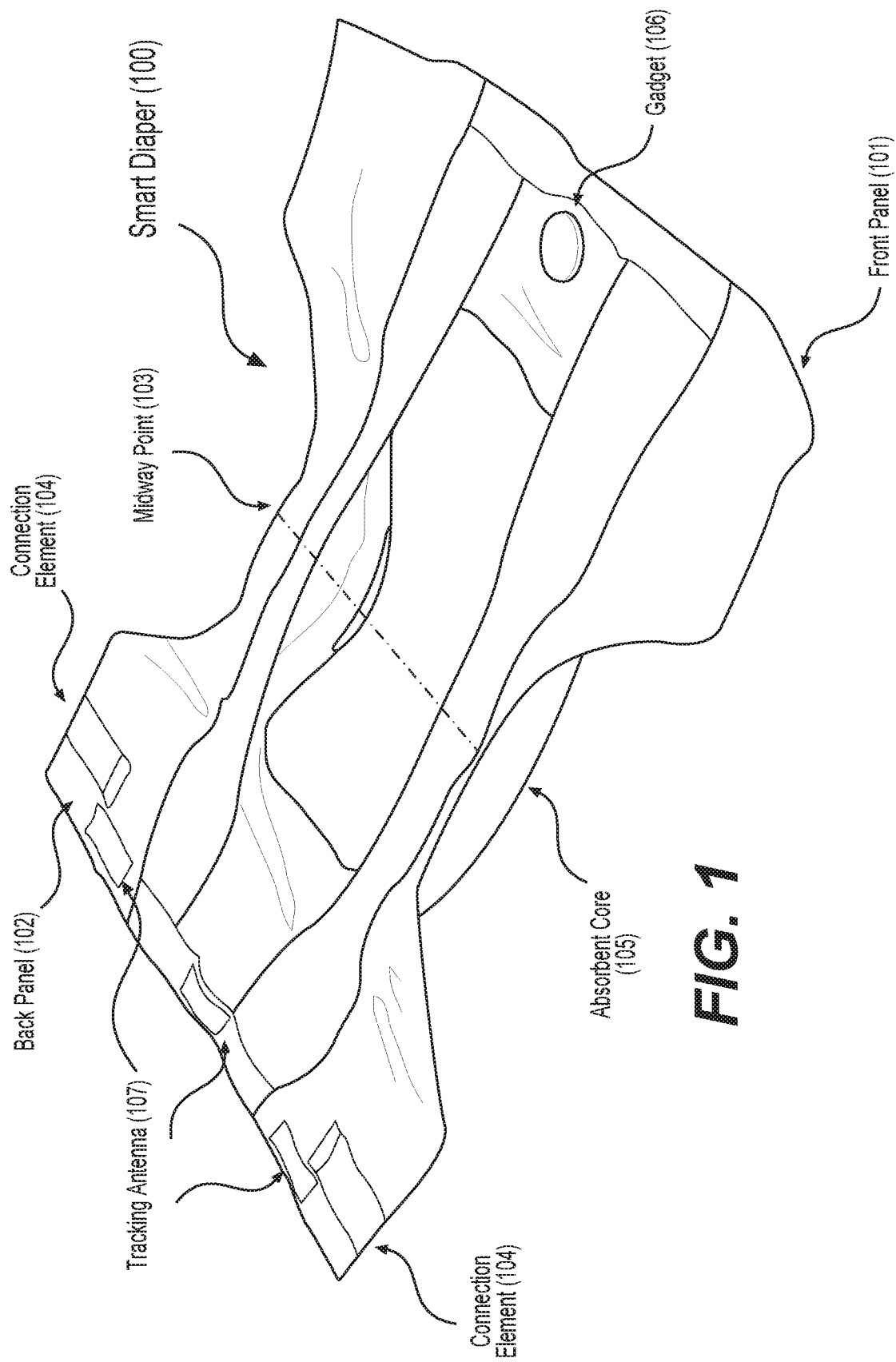
FIG. 1 illustrates an example smart diaper according to an example embodiment.

The smart diapers of these disclosures can include any type of diaper or nappy known to the persons of ordinary skill in the art. FIG. 1 illustrates an example smart diaper according to an example embodiment. In this embodiment, the smart diaper 100 includes a front panel 101 and a back panel 102. The front panel 101 is connected to the back panel 102 at a midway point 103 to form a one-piece article. In other embodiments, the smart diaper 100 can be a one-piece article, which includes only one panel. Other arrangements are also conceivable by one of ordinary skill in the art.

In some embodiments, the smart diaper 100 can include at least one connection element 104, which can be a tape, loop and hook element, etc. The connection element 104 can be attached either to the front panel 101 or to the back panel 102. A caretaker (or a wearer) can position the front panel 101 on the crutch region and the back panel 102 on the bottom region of a wearer, and secure the panels 101 and 102 around the wearer's waste using the at least one connection element 104.

Each smart diaper includes an inside and an outside. Similarly, each panel includes an inside and an outside. In the example embodiment of FIG. 1, the outside of the smart diaper 100, which shows the outside of front panel 101 and the outside of the back panel 102 is depicted. On the inside of the front panel 101 and/or on the inside of the back panel 102, an absorbent core 105 is provided, which can absorb and retain human waste. In this context, human waste can include urine, bowel movement, feces, liquids, moisture, etc.

The smart diaper 100 can also include a gadget 106, which in this example embodiment, is mounted on the outside of the front panel 101. The gadget 106 is discussed in more detail below. The smart diaper 100 can also include one or more tracking antennas 107, which in this example embodiment are mounted on the outside of the back panel 102. In another example embodiment, the antennas 107 can be provided on the sensor pad. Other positions for placing the antennas 107 are also conceivable, e.g., the back panel 102 or both the front panel 101 and the back panel 102. Although not illustrated in FIG. 1, the antennas 107 can be electrically connected to the gadget 106.

Figure 2:
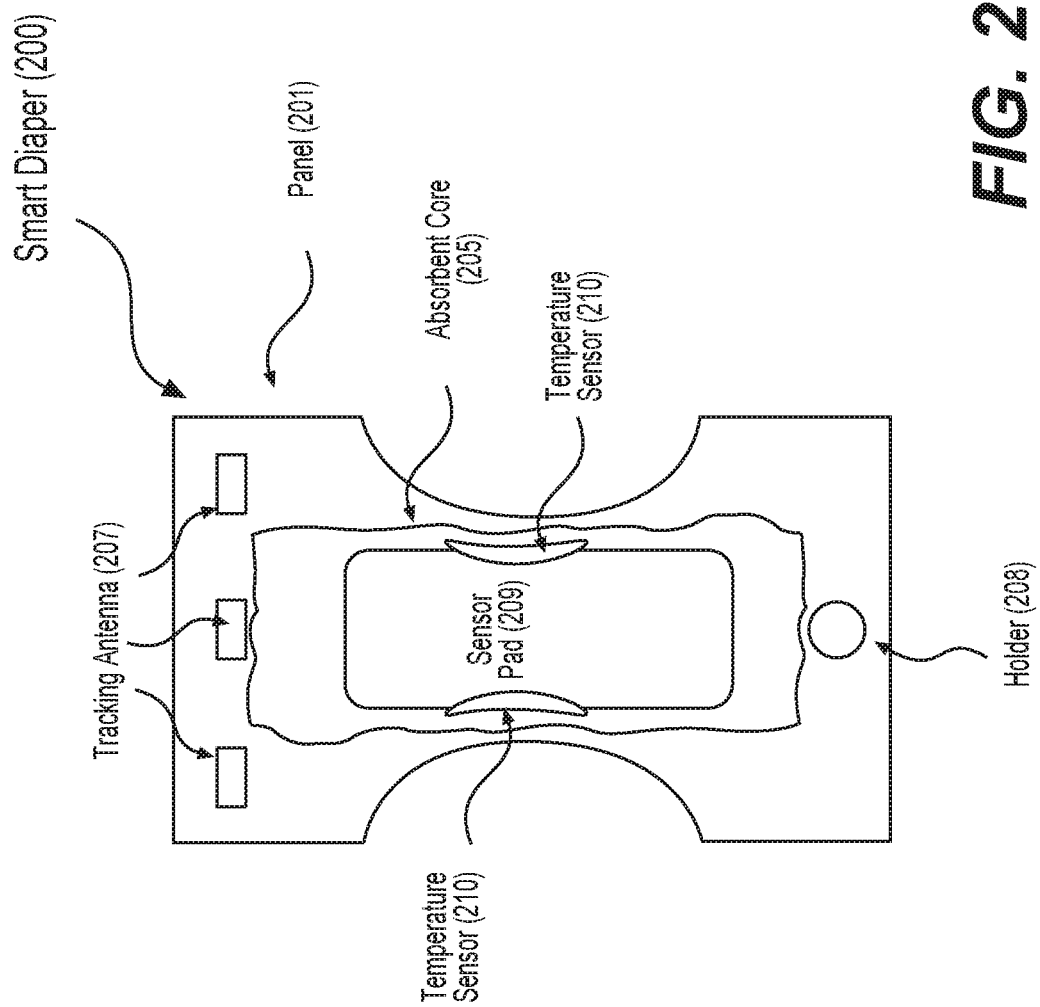
FIG. 2 illustrates another example smart diaper according to an example embodiment.

FIG. 2 illustrates another example smart diaper according to an example embodiment. In this embodiment, the smart diaper 200 includes a panel 201. FIG. 2 depicts the inside of the smart diaper 200 and the inside of the panel 201. In this example embodiment, the tracking antennas 207 are mounted on the inside of the panel 201. The smart diaper 200 can also include a holder 208, which is configured to hold the gadget on the outside of the diaper 200. The smart diaper 200 can further include an absorbent core 205, which can include a sensor pad 209 and one or more temperature sensors 210. The sensor pad 209 can be located on top of, inside, or underneath the absorbent core 205. Similarly, the temperature sensors 210 can be located on top of, inside, or underneath the absorbent core 205. The temperature sensors 210 can be located on the sensor pad 209 or it can be a free standing component.

Although not illustrated in FIG. 2, the antennas 207 can be electrically connected to the sensor pad 209, which in turn is electrically connected to the gadget.

The Sensor Pad

An example smart diaper of these disclosures can be provided with a detection mechanism for detecting moisture, liquids, urine, or human waste. The detection mechanism can be located on, inside, or underneath the absorbent core of the smart diaper. In an example embodiment, the detection mechanism can be a moisture, liquid, or wetness detection sensor.

In an example embodiment, the detection sensor can be a sensor pad. The sensor pad can include at least one sheet of absorbing paper. The at least one sheet of absorbing paper can be a folded sheet of absorbing paper. The folded sheet of absorbing paper forms a three dimensional object, which can detect moisture or liquids in a three dimensional space (as opposed to an unfolded sheet which can detect moisture or liquids only in a two dimensional area).

Figure 3:
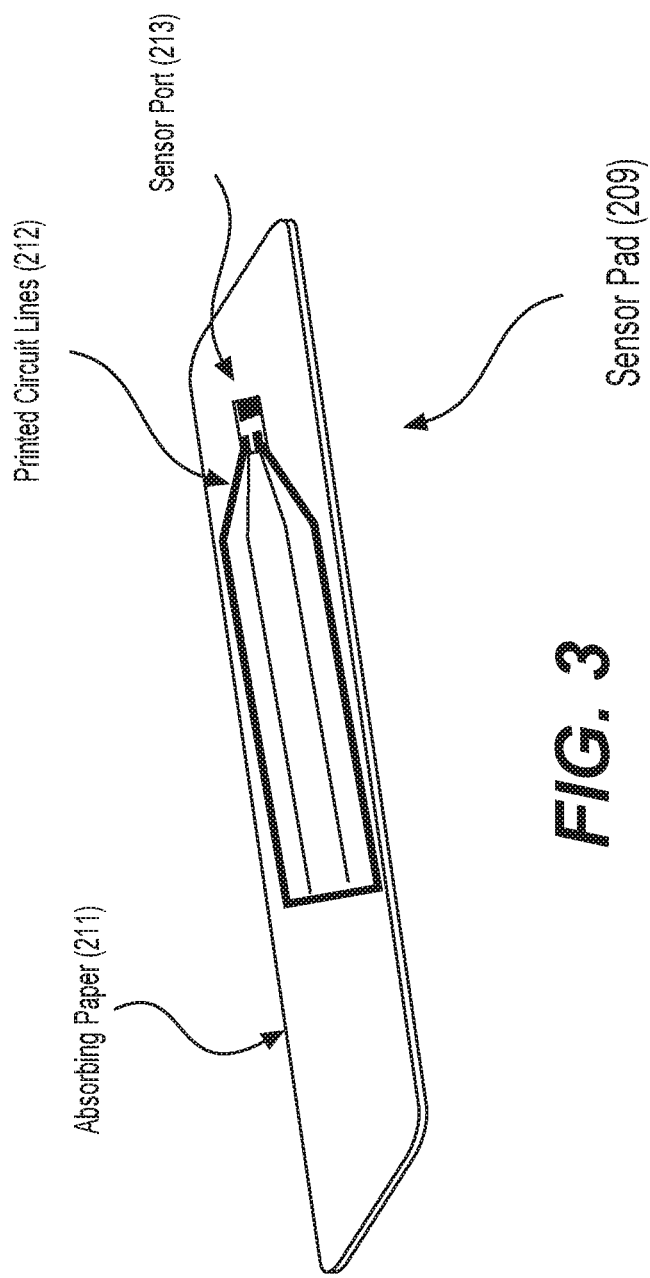
FIG. 3 illustrates an example embodiment of a sensor pad.

FIG. 3 illustrates an example embodiment of a sensor pad. The sensor pad 209 can include a sheet of absorbing paper 211, which can be made of soft paper. The sensor pad 209 can also include various printed circuit lines 212. A circuit line (or loop) is a continuous electrical connection of a conductive material, which is drawn onto, attached to, or connected to the absorbing paper. For example, the circuit lines can be printed on a sheet of absorbing paper using a silver nanoparticle ink. As another example, the circuit lines can be conductive tapes attached to a sheet of absorbing paper. Other means of creating circuit lines are conceivable as well. The circuit lines can have any shape, e.g., straight, circular, curvy, etc. The sensor pad 209 can also include a sensor port 213.

Figure 4:
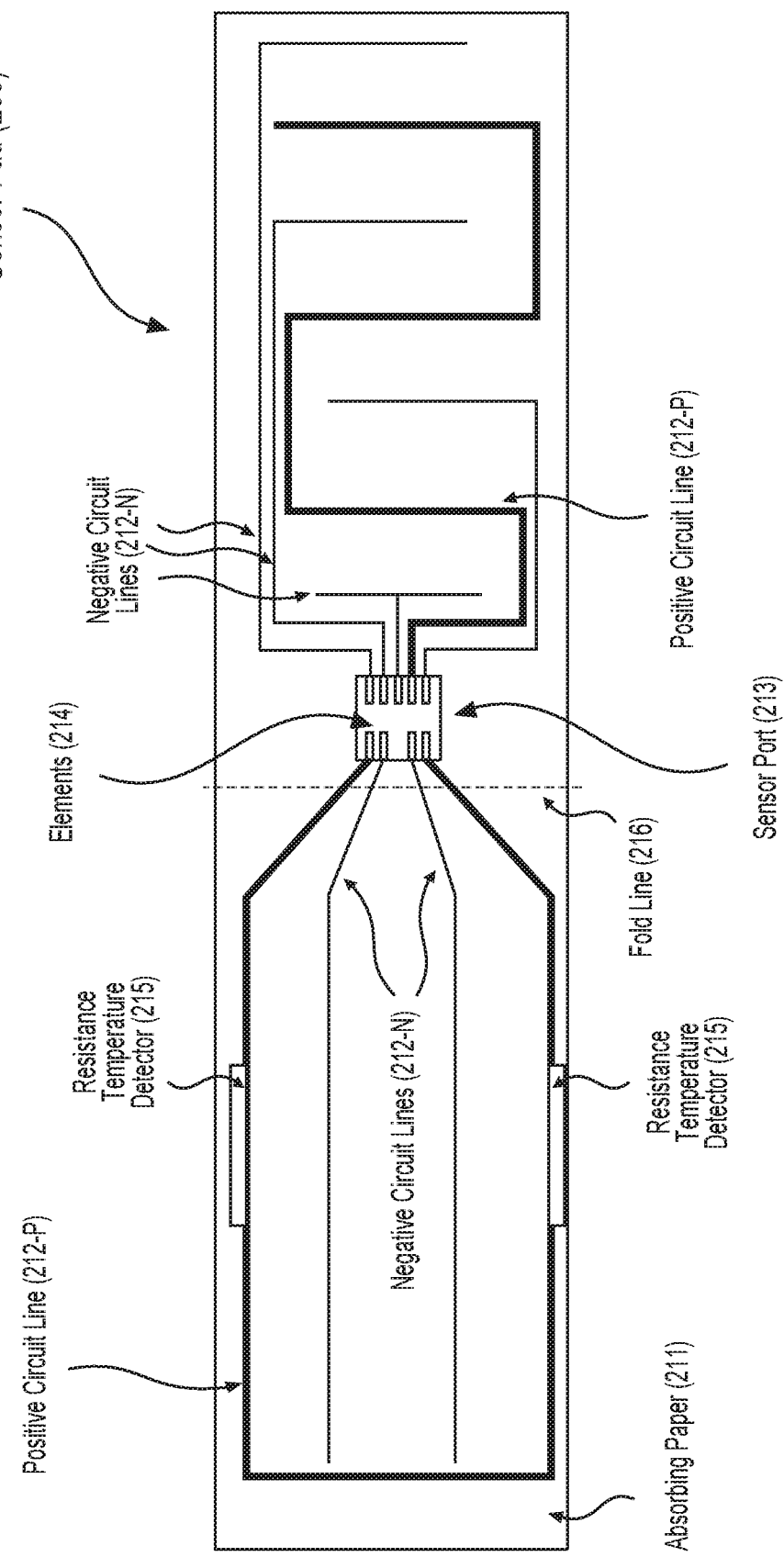
FIG. 4 illustrates another example embodiment of a sensor pad including positive circuit lines and negative circuit lines.

In an example embodiment, there can be two types of circuit lines: positive circuit lines and negative circuit lines. A positive circuit line never crosses a negative circuit line, but a positive circuit line can cross other positive circuit lines, and a negative circuit line can cross other negative circuit lines. FIG. 4 illustrates another example embodiment of a sensor pad including positive circuit lines and negative circuit lines. In FIG. 4, the sensor pad 209 can include various circuit lines 212, including positive circuit lines 212-P and negative circuit lines 212-N, printed on at least one side of the absorbing paper 211. The circuit lines 212 of FIG. 4 are only an exemplary design of an embodiment of circuit lines according to these disclosures. Other arrangements of circuit lines not illustrated in the figures are also within the scope of the present disclosures. For example, in some embodiments, some circuit lines can be thicker lines, and some can be thinner lines.

Each circuit line is electrically connected to an element of a sensor port. The sensor port can include at least two elements. In FIG. 4, for example, the circuit lines 212 are connected to the sensor port 213, which includes 9 elements 214. Additionally, in the sensor pad 209 one or more resistance temperature detectors 215 are provided, which is discussed below.

The sensor pad 209 in FIG. 4 includes a fold line 216. The sensor pad 216 can be folded along the fold line 216 and thus become a three-dimensional sensor, which can detect moisture or human waste in a three-dimensional volume.

In an example embodiment, the positive circuit lines are connected to a first element, and the negative circuit lines are connected to a second element. When the sheet of absorbing paper is exposed to human waste, a positive circuit line and a negative circuit line are short circuited, thereby creating a conductive loop between the first element of the sensor port, the positive circuit line, the negative circuit line, and the second element of the sensor port. Therefore, if a signal is transmitted from the first (or second) element, the signal can be detected at the second (or first) element.

Figure 5:
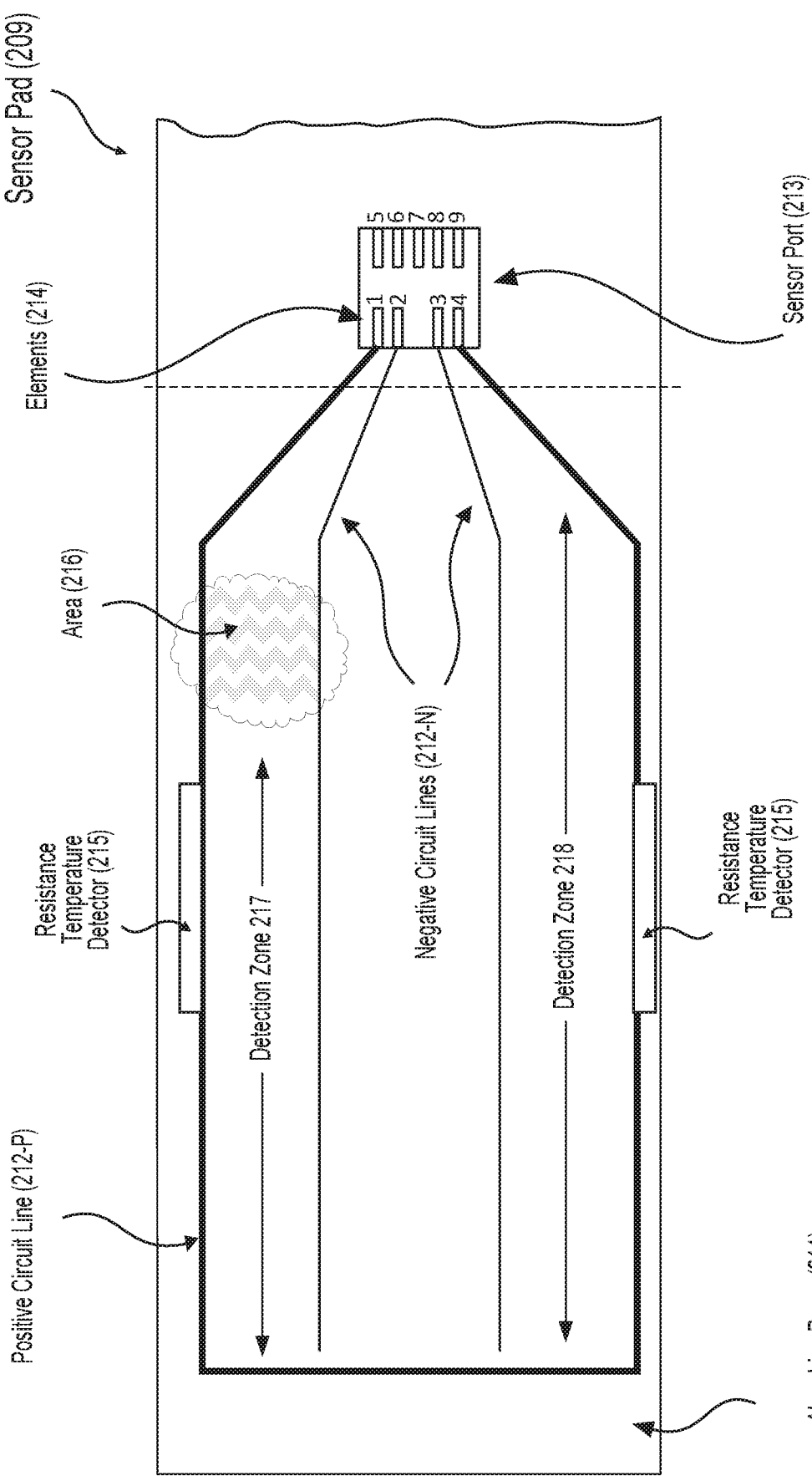
FIG. 5 illustrates yet another example embodiment of a sensor pad including positive circuit lines and negative circuit lines.

FIG. 5 illustrates yet another example embodiment of a sensor pad including positive circuit lines and negative circuit lines. In this example embodiment, only one part of the sensor pad 209 is depicted. Nevertheless, the positive circuit line 212-P is connected to elements 1 and 4 of the sensor port 213, and negative circuit lines 212-N are connected to elements 2 and 3 of the sensor port 213. An area 216 of the sensor pad 209 is exposed to human waste, thereby creating a path for conduction of electric current between the positive circuit line 212-P (which is connected to element 1) and the negative circuit line 212-N (which is connected to element 2). Therefore, if a signal is transmitted from element 1 (or 2), the signal would be received at element 2 (or 1).

In an example embodiment, a sensor pad can include several detection zones. A detection zone is an area of the sensor pad that if exposed to human waste, the exposure can be detected by a gadget and the gadget can identify the exposed detection zone. Identifying the detection zone that is exposed to human waste can be beneficial for various reasons. For example, using detection zones, the gadget can determine how much human waste is present in the smart diaper. This is because the more waste is present in the smart diaper, the more detection zones are short circuited. Moreover, generally, babies urinate on the front panel of the diaper; however, feces can be found on the back panel of the diaper. Thus, depending on the identity of the detection zone, the gadget can predict the type of human waste present in the diaper.

As such, each detection zone can include a positive circuit line and a negative circuit line dedicated to the detection zone. Therefore, when human waste is present in the detection zone, the positive circuit line and the negative circuit line dedicated to the detection zone can be short circuited, and hence the gadget can identify the zone at which human waste is present. Alternatively, each detection zone in the diaper can include a positive (or negative) circuit line dedicated to the detection zone, and a negative (or positive) circuit line shared by all the detection zones. By sharing the circuit line, fewer elements are needed at the sensor port thereby minimizing the size of the sensor port. Therefore, when human waste is present in any detection zone, the circuit line dedicated to the detection zone and the other line shared by all the detection zones can be short circuited. The gadget in turn can identify the detection zone by identifying the circuit lines that are short circuited, and hence, can provide this information to the caretaker.

For example, in FIG. 5, two detection zones are depicted: detection zone 217 and detection zone 218. The detection zone 217 is identified by the positive circuit line 212-P, which is connected to elements 1 and 4, and the negative circuit line 212-N, which is connected to the element 2 of the sensor port 213. The detection zone 218 is identified by the positive circuit line 212-P, which is connected to elements 1 and 4, and the negative circuit line 212-N, which is connected to the element 3 of the sensor port 213. In this example embodiment, the positive circuit line 212-P is shared by detection zones 217 and 218. The area 216, which represents an exposure to human waste, is located in the detection zone 217. Because of the exposure, the positive circuit line 212-P and the negative circuit line 212-N (connected to element 2) are short circuited, and therefore, a signal transmission at the elements 1 or 4 can be detected at the element 2. However, a transmission at any of the elements 1, 2, and 4 would not result in a detection of the signal at the element 3. Therefore, the gadget can conclude that human waste is present at the detection zone 217, and transmit this information to the caretaker. Alternatively, the gadget can transmit the information relating to which elements are short circuited, and the device paired with the gadget can make the analysis.

In yet another embodiment, the sensor pad includes several circuit lines. Each circuit line is connected to an element of the sensor port of the sensor pad. The gadget is configured to transmit test signals to each one of the elements. Upon transmission of a signal to an element, the gadget is configured to detect the test signals at the other elements of the sensor port. If a test signal is detected, the gadget identifies the element of the sensor port through which the test signal was transmitted and the element of the sensor port through which the test signal was detected. The gadget is configured to transmit this information to the caretaker. Based on this information, the caretaker or a device used by the caretaker can determine which zone of the sensor pad is short circuited, and therefore, other information can be displayed based on this determination.

In an example embodiment, the surface of the sensor pad can be provided with a layer of salt to facilitate detection of moisture. Certain liquids, such as water, have poor conductivity. By applying a layer of salt, for example, when the sensor pad is exposed to water, the short circuiting of the circuit lines can be facilitated and the presence of the water can be detected easier.

Although in describing the printed circuit lines 212, the phrases "positive circuit line" and "negative circuit line" were used in these disclosures, these words are only chosen to facilitate naming of these components, and these phrases do not describe any characteristics of the signals that may be transmitted or detected through these circuit lines. As such, these words can be interchangeable or replaced with other words without affecting the scope of these disclosures.

Temperature

The smart diaper of these disclosures can include a temperature detection mechanism. In an example embodiment, the detection mechanism can determine the temperature of the wearer's body, skin, or any human waste expelled by the wearer. In an example embodiment, the detection mechanism includes a sensor pad, which in addition to circuit lines, can include a resistance temperature detector ("RTD"). An RTD is a temperature sensor that contains a resistor that changes resistance value as its temperature changes. Generally, an RTD consists of a length of fine coiled wire wrapped around a ceramic or glass core. The RTD's coiled wire is made from a pure material whose resistance at various temperatures has been documented. The material has a predictable change in resistance as the temperature changes; it is this predictable change that is used to determine temperature. RTDs are the most accurate temperature sensors, and provide excellent stability and repeatability.

In an example embodiment, the RTD is located on an RTD circuit line that is electrically connected to a third element of the sensor port on one end, and electrically connected to a fourth element of the sensor port on the other end. Using the third and fourth elements of the sensor port, the gadget is configured to detect the resistance of this line continuously or intermittently. In another example embodiment, the RTD can be located on a positive or negative circuit line that is connected to a first element of the sensor port on one end, and to a third element of the sensor port on the other end. Similarly, in this embodiment, using the first element of the sensor port and the third element of the sensor port, the gadget is configured to detect the resistance of this line continuously or intermittently. Other arrangements of the RTD circuit line are also possible and conceivable to one of ordinary skill in the art.

In FIG. 5, two RTDs 215 are provided, each of which is located on the positive circuit line 212-P. In this example embodiment, a continuous or intermittent determination of the resistance of the positive circuit line 212-P, using the elements 1 and 4, can provide an estimate of the wearer's body temperature (or waste temperature), and therefore inform the caretaker about any fluctuations in the body temperature.

In an example embodiment, the RTD circuit line can be used by the gadget to determine the orientation of the gadget. For example, the RTD circuit line can be electrically connected to a first element and a second element of the sensor port. However, a third element and a fourth element of the sensor port are not connected to each other using a circuit line. Upon attachment of the gadget to a diaper, using the first element of the sensor port, the gadget is configured to send a test signal. If the test signal is detected at the second element of the sensor port, the gadget determines that the gadget is properly connected to the sensor port. However, if the gadget is improperly connected (i.e., upside-down), the transmission of the test signal would take place at the fourth element of the sensor pad, and the test signal would not be detected at the third element of the sensor pad. Therefore, the gadget can determine that the orientation of its connection to the sensor pad is improper. While this feature of these disclosures was described with respect to an RTD circuit line, one of ordinary skill in the art recognizes that any circuit line (i.e., feedback loop) that is asymmetrically connecting two elements of the sensor port can be used for this purpose.

The Gadget

Figure 6:
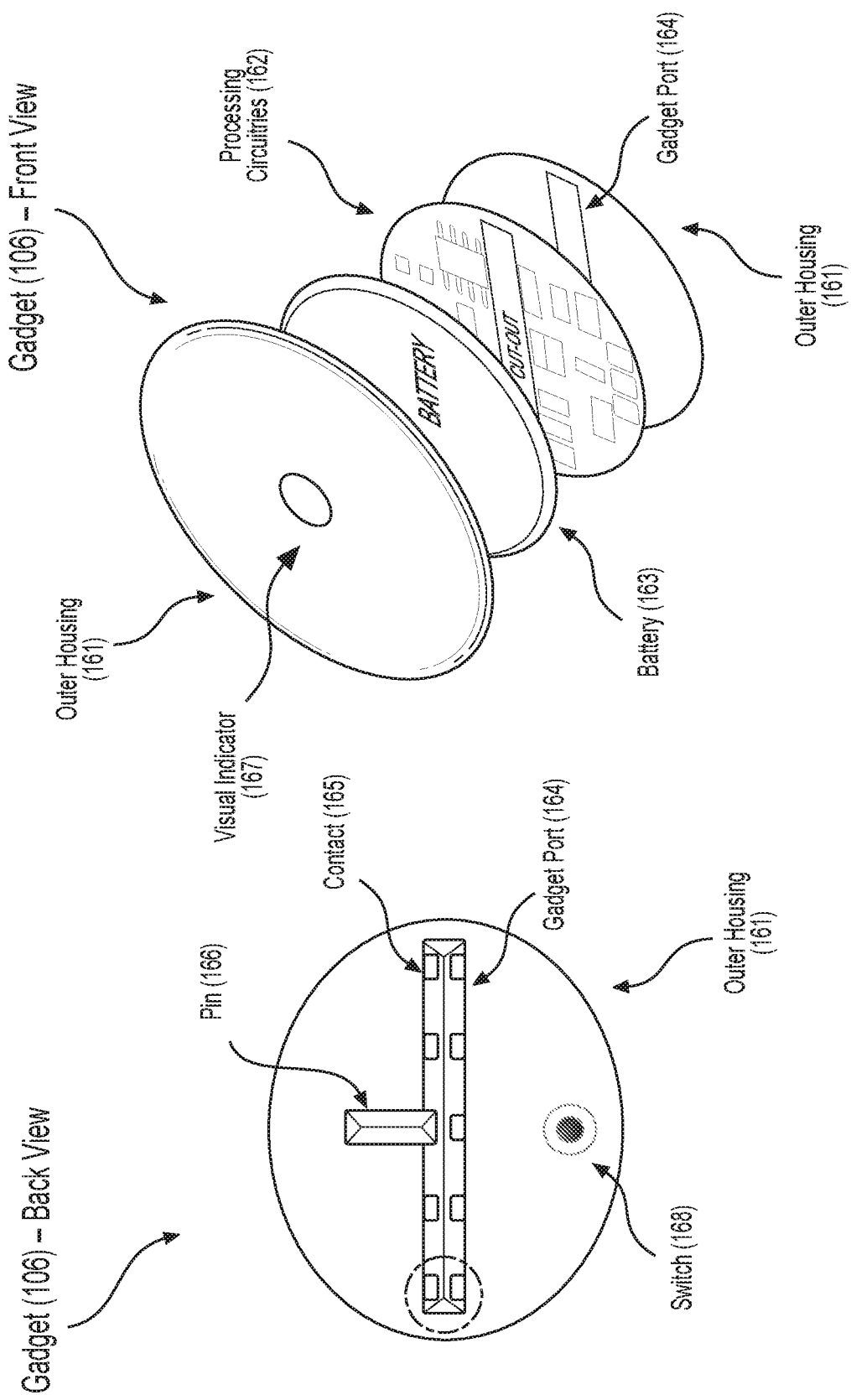
FIG. 6 represents a front view and a back view of an exemplary gadget according to an example embodiment.

The gadget according to the present disclosures can include an outer housing, in which there are processing circuitries and a battery. FIG. 6 represents a front view and a back view of an exemplary gadget according to an example embodiment. The gadget 106 includes an outer housing 161. Inside of the outer housing 161, processing circuitries 162 and a battery 163 are located. The processing circuitries 162 include a processor, a memory device, and a transceiver. The battery 163 can be any one of the following types of batteries: Lithium Ion, Lithium Polymer, Nickel Cadmium, and Nickel Metal Hydride. Other types of batteries are also conceivable to one of ordinary skill in the art.

The outer housing can include a gadget port for receiving a connector. The connector can be configured to electrically connect (or couple) the gadget to the sensor port of the sensor pad. In an example embodiment, the gadget port can be located on the back or front of the outer housing. Alternatively, the gadget port can be placed on any one of the sides of the outer housing. The example embodiment of FIG. 6 includes a gadget port 164, which is located on the back of the gadget 106. The gadget port 164 can include at least one contact 165 for electrically connecting the gadget 106 to the connector.

The gadget can also include a lock mechanism which is configured to hold the gadget to the connector or to the smart diaper. It is assumed that regular movements of the wearer of the smart diaper can cause detachment or disengagement of the gadget and therefore, it is desired to prevent such detachment or disengagement. In addition, a baby might be curious to play with the gadget, and therefore, it would be desirable to fasten or secure the gadget to the smart diaper or the connector. Various lock mechanisms can be implemented for this purpose. In an example embodiment, the connector and the gadget are configured to be fastened or secured to each other. For example, the connector is provided with a hole and the gadget port of the gadget includes a movable pin to be secured in the hole when the connector is inserted into the gadget. The pin can be secured in the hole using an elastic force, or the pin can be mechanically coupled to a button for movement. FIG. 6 depicts an example pin 166 which can secure the gadget 106 to the connector. Other lock mechanisms are also conceivable. For example, it is possible to secure the gadget on the smart diaper by using a magnetic connection, hook and loop connection, tape, etc.

In some embodiments, the battery of the gadget is replaceable. In some embodiments, the battery of the gadget is not rechargeable. In other embodiments, the battery can be rechargeable, and the charge for the battery can be provided through a charging port. In some embodiments, the outer housing can include the charging port for supplying energy and communicating information to the processing circuitries of the gadget. In some embodiments, the charging port can be the same as the gadget port which receives the connector. Yet in other embodiments, the charging port can be separate from the gadget port. FIG. 6 illustrates an example charging port 164 according to an example embodiment. In this example embodiment, the gadget port is the same as the charging port. The charging port 164 can be located on the back of the outer housing and is connected to the battery 163. Alternatively, the charging port 164 can be placed on any one of the sides or front of the outer housing. Using the charging port 164, in addition to charging the battery 163, the caretaker can electrically connect the gadget 106 to other devices, such as a laptop, desktop, tablet, cellphone, etc., and manipulate the software stored on the processing circuitries 162 of the gadget. Alternatively, manipulation of the software stored on the processing circuitries 162 can be done using a wireless connection, e.g., Wi-Fi or Bluetooth connection.

Yet in other embodiments, the battery can be rechargeable and the battery can be charged wirelessly or inductively. Inductive charging takes advantage of the principles of electromagnetic induction to transfer electric energy from a base to the gadget without any electric connection. Accordingly, the base is provided with an induction coil to create an alternating electromagnetic field from within the base. A second induction coil is provided in the gadget, which is configured to take power from the electromagnetic field, and convert it back into electric current to charge the battery. In effect, the two induction coils in proximity combine to form an electrical transformer. In the embodiments provided with inductive charging, the user of the gadget can place the gadget over, by, or within a vicinity of the base. Subsequently, the gadget determines that the gadget is placed over, by, or within the vicinity of the base and begins receiving charge from the base. Although charging using a charging port and charging inductively are described separately, in certain embodiments the gadget can be capable of being charged both inductively and by using a charging port.

In some embodiments, the gadget can be provided with a visual indicator. The gadget is configured to provide visual signals to the caretaker using the visual indicator. For example, the visual indicator can alert the caretaker that the battery charge is low, or that the smart diaper needs to be changed. The visual indicator can be located anywhere on the outer housing. The visual indicator can be a light source or a display screen. The light source can be any of the following light sources: Compact Fluorescent (CFL), Light Emitting Diode (LED), Incandescent, Fluorescent, and Halogen. Other types of light sources are also conceivable to one of ordinary skill in the art. For example, in FIG. 6, the visual indicator 167 is an LED light bulb, which is electrically coupled to the battery 163 and the processing circuitries 162.

The display screen can be an OLED, AMOLED, e-Ink, color paper ink, or other display screens known to persons of ordinary skill in the art. The display screen can be a touchscreen device, which can enable the gadget to receive touch commands from the user. A touch command can include performing one of the following actions on the screen of the gadget: tapping, double tapping, swiping, long pressing, long-press and dragging, double-tap dragging, pinching open, pinching closed, two finger touching, two finger swiping, two finger long-pressing, two finger long-press swiping, two finger double tapping, and two finger rotating.

In some embodiments, the outer housing can be provided with one or more buttons or switches for the caretaker to communicate with the gadget. For example, on the outer housing of the gadget one or more buttons can be provided to turn off the gadget, to activate the Bluetooth or Wi-Fi discoverability mode of the gadget, or to perform functions relating to the visual indicator. FIG. 6 illustrates an exemplary switch 168 provided on the outer housing 161 of the gadget 106. In an example embodiment, by pressing the switch 168, the caretaker can turn off the gadget 106. Other functionalities are also conceivable. For example, by holding the switch 168 for a few seconds, the discoverability mode of the gadget 106 can be activated.

The gadget can be configured to be paired with another device ("Smart Device"), which can be a smartphone, cell phone, a laptop, a desktop, a notebook, a tablet, a wearable device, etc. Pairing the gadget with the Smart Device establishes an initial bonding between the gadget and the Smart Device so that communication is allowed and facilitated between the two devices. In an example embodiment, the gadget can use Bluetooth wireless technology standard or Wi-Fi technology standard for exchanging data and communication between the gadget and the Smart Device. In another example embodiment, the gadget can use Bluetooth wireless technology standard for exchanging data and communication between the gadget and a hob. The hob can have a Wi-Fi connection to a router or a cellular connection. Both the router and the hub are connected to a network, such as the Internet. Using the network, the gadget can exchange data and communicate with the Smart Device. Other wireless technology standards such as Induction Wireless, Infrared Wireless, Ultra Wideband, ZigBee, or a combination thereof are also conceivable.

In an example embodiment, during pairing, a link key is used, which can be a shared secret known between the gadget and the Smart Device. If both devices store the same link key, they are said to be paired or bonded. In some embodiments, it is possible to limit the communication of the gadget only to a Smart Device that was previously paired with the gadget. Such limitation can be implemented by cryptographical authentication of the identity of the Smart Device by the gadget to ensure that the Smart Device is the Smart Device that was previously paired with the gadget. Protection against eavesdropping is also possible by encrypting the exchanged data between the gadget and the Smart Device. Users can delete link keys from either device, which removes the bond between the devices. It is possible for one device to have a stored link key for a device with which it is no longer paired.

Figure 7:
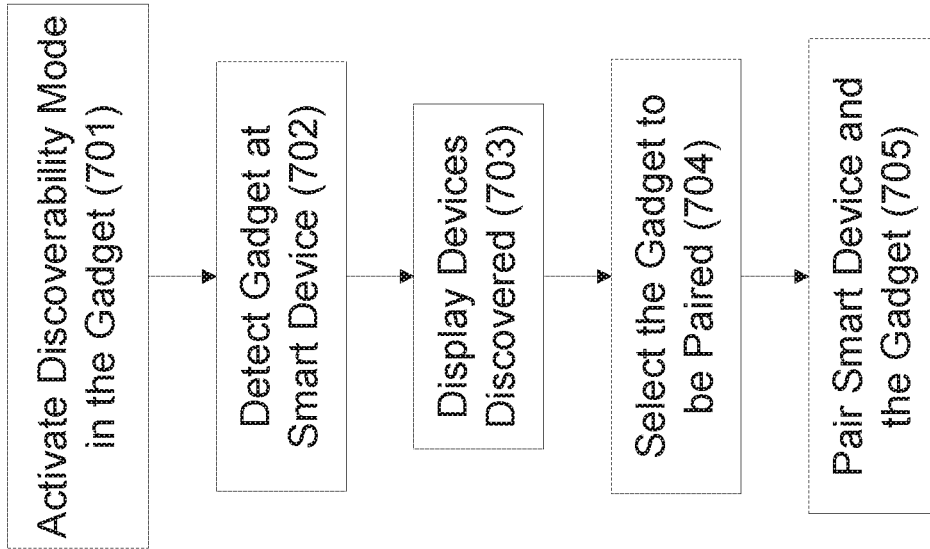
FIG. 7 shows an example flow process for pairing a gadget with a Smart Device.

FIG. 7 shows an example flow process for pairing a gadget with a Smart Device. In this example embodiment, pairing can start by the caretaker initiation of the discoverability mode in the gadget in step 701. In the discoverability mode, the Smart Device can detect the gadget and let the user know the identity of the gadget, for example, by displaying it. The discoverability mode, for example, can be initiated by pressing the switch 168 in FIG. 6 for a few seconds. In step 702, the user can request the Smart Device to detect the devices around the Smart Device. For example, the user can make the detection request by choosing an "Add a Bluetooth Device" or "Add a Wi-Fi Device" on the Smart Device. Subsequently, the Smart Device seeks gadgets (and other devices) close to the Smart Device and at step 703 displays the identity of any gadgets (and other devices) discovered by the Smart Device. At step 704, the user can select the gadget that the user intends to pair with the Smart Device. At step 705, the Smart Device can form a bond between the gadget and the Smart Device, and the gadget and the Smart Device will be able to communicate thereafter. Over the subsequent interactions, the gadget and the Smart Device can connect to each other by reverting to the bond that has already been established. The user can sever the bond (i.e., deleting the link key) at any time, thereby terminating the communication link between the gadget and the Smart Device.

Connector and Connection to the Sensor Pad

The smart diaper of the present disclosures can comprise a connector for electrically connecting the sensor pad to the gadget. In an example embodiment, the connector includes various circuit lines each of which is configured to electrically connect each element of the sensor port to a respective contact of the gadget port. In an example embodiment, the connector can include a sheet of paper on which various circuit lines are printed. In an example embodiment, the sheet of paper can be constructed from thick paper.

Figure 8:
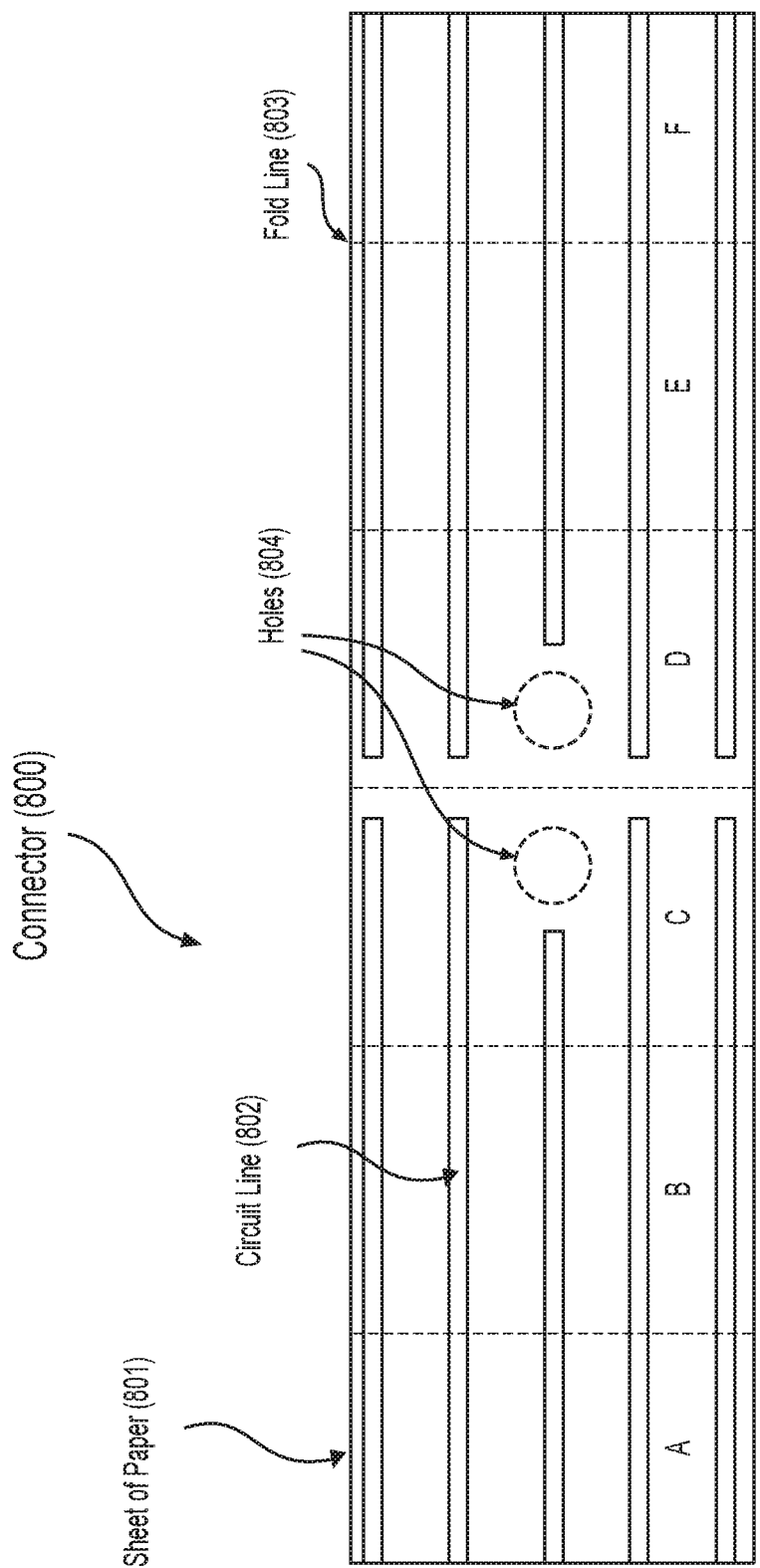
FIG. 8 illustrates an example connector according to an example embodiment.
Figure 9:
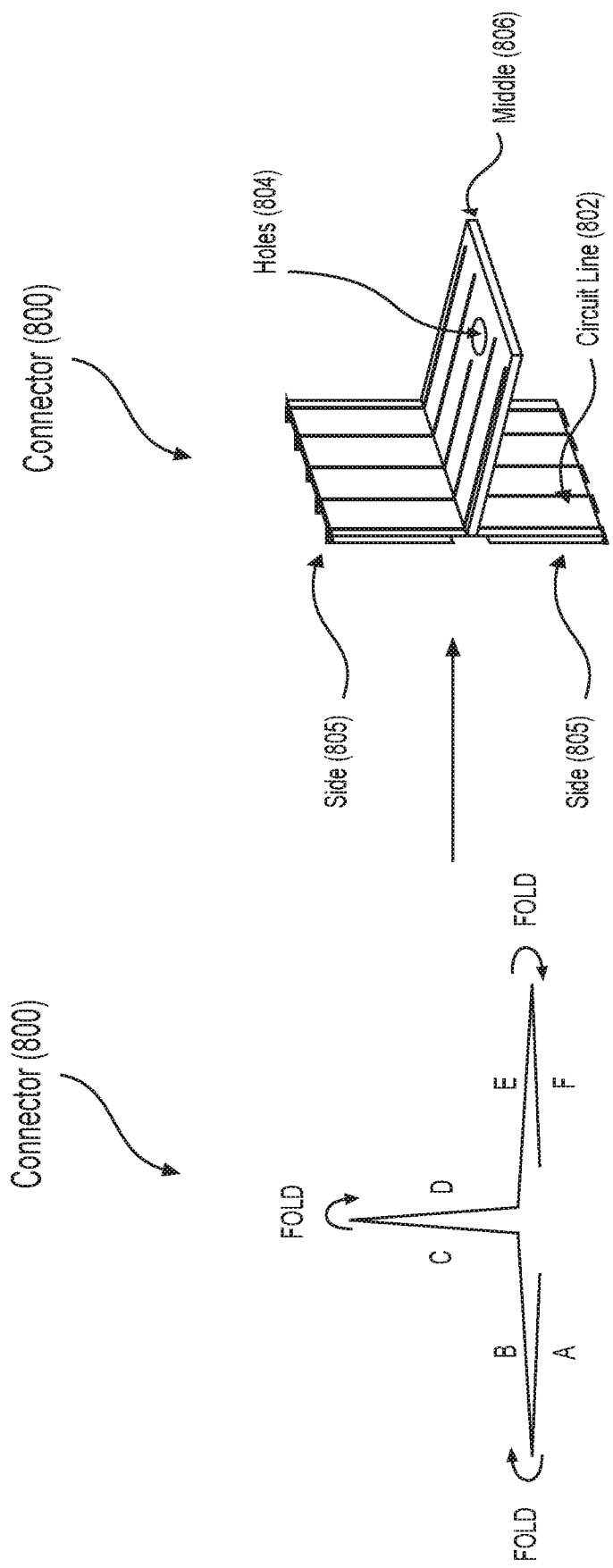
FIG. 9 illustrates an example connector folded according to an example embodiment.

FIG. 8 illustrates an example connector according to an example embodiment. In this embodiment, the connector 800 includes a sheet of paper 801, on which various circuit lines 802 are printed. The circuit lines can be printed on the sheet 801 using a silver nanoparticle ink. In some embodiments, one or more fold lines 803 can be designated. The fold lines can be perforation lines. In some embodiments, one or more holes 804 can be cut out. These holes can be used by the pin 166 to fasten or secure the gadget 106 to the connector 800 and the smart diaper 100. FIG. 9 illustrates an example connector folded according to an example embodiment. In this embodiment, the connector 800 is folded along the fold lines 803. The folded connector 800 included two sides 805, and a middle 806. The sides 805 are configured to attach to a sensor port of a sensor pad, and the middle 806 is configured to be inserted into a gadget port of a gadget.

Figure 10:
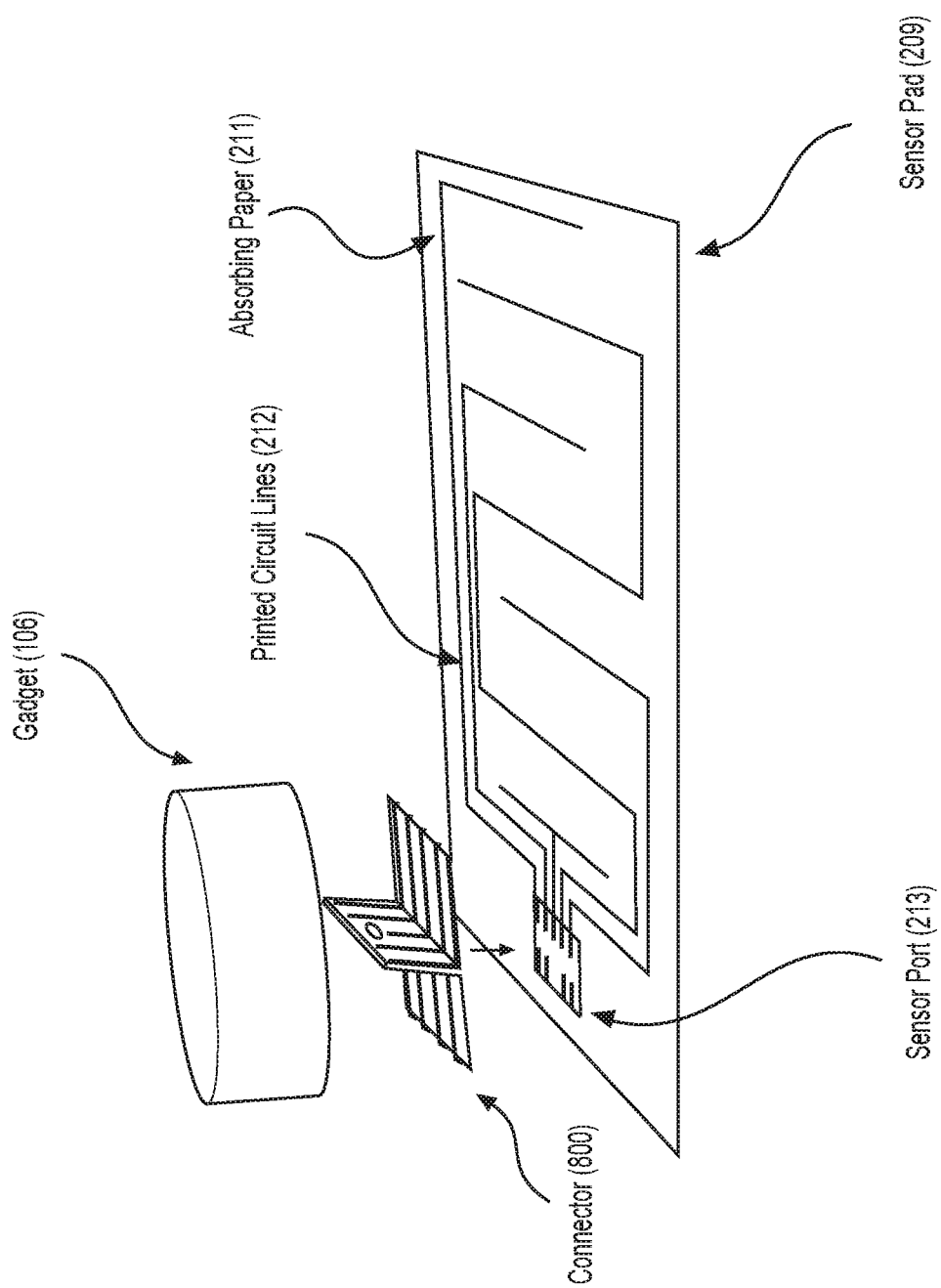
FIG. 10 illustrates an example assembly of a gadget, connector and sensor pad according to an example embodiment.

FIG. 10 illustrates an example assembly of a gadget, connector and sensor pad according to an example embodiment. In this example embodiment, the gadget 106, the connector 800, and the sensor pad 209 are mounted on top of each other. The sensor pad 209 can be located in the absorbent core 105 of the smart diaper 100. The connector 800 can be attached to the sensor port 213 of the sensor pad 209 so that each of the elements of the sensor port 213 is electrically connected to a respective circuit line of the connector 800. In certain embodiments, chemical compounds can be added to each circuit line or element of the sensor port to facilitate contact and conductivity of current. In some embodiments, an adhesive can be added between the connector 800 and the sensor port 213 to ensure that the connector 800 is properly secured to the sensor pad 209.

The connector 800 can be inserted into the gadget 106 (or the gadget 106 can be pushed over the connector 800). The gadget 106 and the connector 800 are configured so that once the connector 800 is inserted into the gadget 106, each of the circuit lines of the connector 800 can be electrically connected to the respective one of the contacts of the gadget port of the gadget 106.

FIG. 11A illustrates an example smart diaper before mounting a gadget. In this example embodiment, the connector 800 is provided on the front panel 101 of the smart diaper 100. The connector 800 is assembled on a sensor pad, which is located in the absorbent core of the diaper 100. FIG. 11B illustrates the example smart diaper 100 on the front panel 101 of which a gadget 106 is mounted. In this example embodiment, the gadget 106 is mounted on the front panel 101 using the pin 166.

Figure 12A:
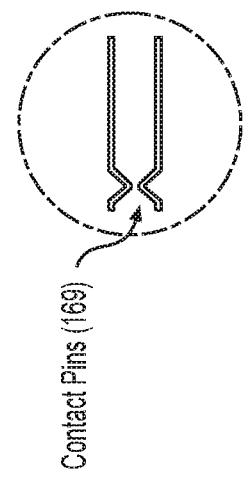
FIG. 12A illustrates an example contact pins with springing characteristic for securing a gadget to a connector.
Figure 12:
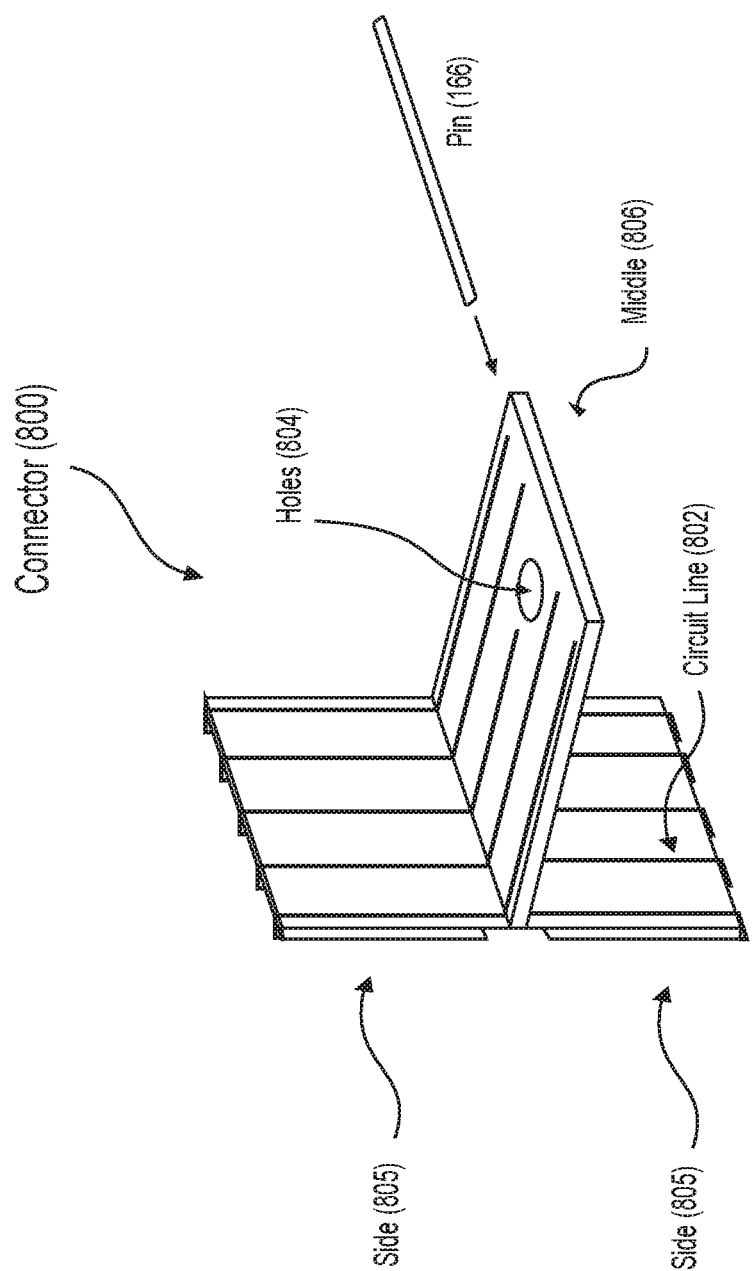
FIG. 12 illustrates an example connector and a pain for securing a gadget to the connector.

FIG. 12 illustrates an example connector and a pain for securing a gadget to the connector. In this example embodiment, the connector 800 is folded so that the sides 805 and the middle 806 can be shaped. Moreover, the holes 804 are aligned so that the pin 166 can pass through the holes 804. Once the connector 800 is inserted into the gadget port of a gadget, the pin 166 of the gadget passes through the holes 804, thereby securing the gadget to the connector 800. While not displayed in FIG. 12, the pin 166 can be mechanically coupled to the gadget 106, and can be positioned in the holes 804 using a button which can mechanically move the pin 166.

FIG. 12A illustrates an example contact pins with springing characteristic for securing a gadget to a connector. In an example embodiment, the contact pins 169 can be secured to the outer housing 161 of the gadget 106. The contact pins 169 can pass through the holes 804 of the connector 800 and, thus can secure the gadget 106 to the connector 800.

The Gadget Software and the Smart Software

The gadget performs the functionalities described herein using a gadget software installed on the gadget. The gadget software provides for interaction with a Smart Device, and is capable of pairing the gadget with the Smart Device. The gadget software is also capable of communicating with the software installed on the Smart Device ("Smart Software"). The Smart Software is also configured to interact with the gadget software.

Figure 13:
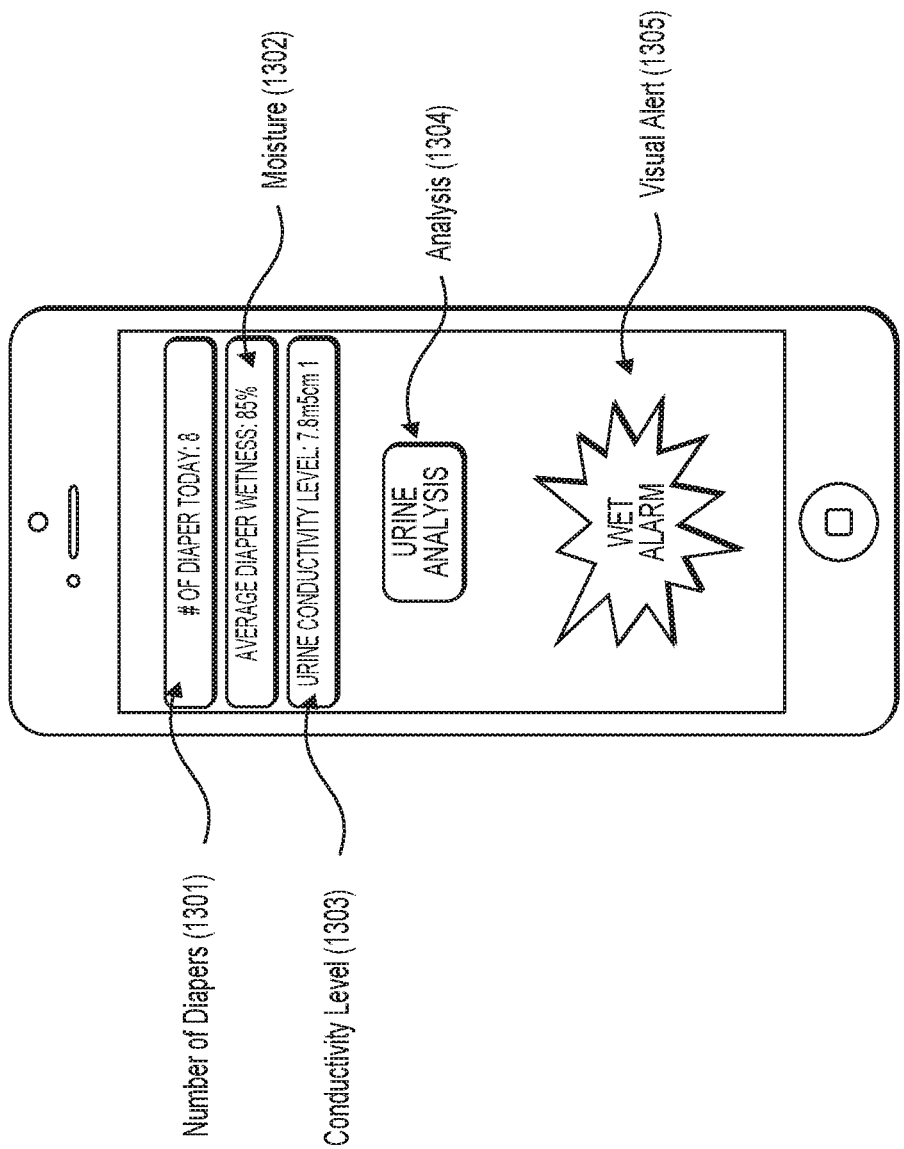
FIG. 13 illustrates an example user interface of a Smart Software according to an example embodiment.

In an example embodiment, the gadget software can communicate the presence of moisture, liquids, or human waste on the sensor pad. In this example embodiment, the gadget software is configured to transmit a test signal, using the processing circuitries of the gadget, through an element of a sensor port connected to a circuit line of a sensor pad. The gadget software is also capable of detecting the test signal, using the processing circuitries of the gadget, at another element of the sensor port connected to another circuit line of the sensor pad. If the gadget software detects the test signal at the other element, the gadget software determines that two separate circuit lines are short circuited, thereby deducing that the sensor pad is exposed to moisture, liquids, or human waste. As a result, the gadget software is configured to transmit or communicate an alert to the Smart Software to notify the caretaker that the diaper bearing the gadget needs to be changed. The Smart Software can notify the caretaker by displaying a visual alert, sound alert, or vibration of the Smart Device. FIG. 13 illustrates an example user interface of a Smart Software according to an example embodiment. In this example embodiment, a user interface for the Smart Software is provided. The user interface is configured to provide a visual alert 1305 to the caretaker. In addition to the visual alert, in some embodiments, the user interface is configured to cause vibration of the Smart Device when the user interface provides the visual alert. While in this example embodiment the Smart Software provides the alerts when the user interface of the Smart Software is running, in some other embodiments, the Smart Software is configured to alert the caretaker even when the user interface is not being displayed.

In an example embodiment, the caretaker can determine how often the test signal is transmitted and detected by the gadget. For example, in the user interface of the Smart Software, there can be an option for setting the mode for transmission and detection of the test signal, and upon clicking on this option, the caretaker can choose the mode. As another example, the caretaker can choose the mode using a button provided on the gadget. There can be several modes of transmission and detection of the test signal. In an example embodiment, the gadget can transmit and detect the test signal continuously. In another example embodiment, the test signal can be transmitted and detected intermittently. For example, the gadget can wait for a predetermined period of time between each two transmissions and detections of the test signal. In yet another example embodiment, the gadget transmits and detects the test signal at random times.

In the example embodiment of FIG. 13, upon initiation of the Smart Software on the Smart Device, certain information can be presented to the caretaker. For example, each time a caretaker changes the wearer's diaper, the caretaker detaches the gadget from the diaper. Each time the gadget is detached from the diaper, the gadget can transmit a message or signal to the Smart Software of the Smart Device indicating a diaper change. The Smart Software can collect this information and display the information to the caretaker. For example, in FIG. 13, a field 1301, number of diapers, is provided which indicates the number of diapers used. In this example embodiment, the daily usage of diapers are indicated; however, by clicking or touching on the field 1301, the caretaker can change the frequency of count to hourly, weekly, monthly, etc.

In another example embodiment, several detection zones are provided on the sensor pad of the smart diaper. After human waste is expelled by the wearer of the smart diaper, the gadget is configured to determine how many of the detection zones are short circuited, and then communicates this information to the Smart Software of the Smart Device. Based on this information, the Smart Software determines a quantity for the human waste present in the smart diaper, and displays this information to the caretaker. For example, as presented in FIG. 13, the Smart Software, in a field 1302, moisture, displays to the user how wet inside of the smart diaper is. The caretaker can touch the field 1302 and request different information to be displayed in regards to the detection zones short circuited. For example, the caretaker can ask the Smart Software to display which detection zones are short circuited.

In yet another example embodiment, the gadget is configured to determine, for each detection zone, the level of conductivity of the human waste, and transmit this information to the Smart Software. Based on this information, the Smart Software can provide certain analysis about the human waste present in the smart diaper. For example, in field 1303, conductivity level, the Smart Software displays a conductivity level for the human waste, and in field 1304, analysis, the Smart Software provides certain analysis about the human waste. For example, in addition to or instead of the conductivity level, the Smart Software can display certain information relating to urine osmolality, sodium, acidity, and uncharged glucose. This list is not exhaustive and other information obtainable by measuring the conductivity of the human waste can also be displayed.

Figure 14:
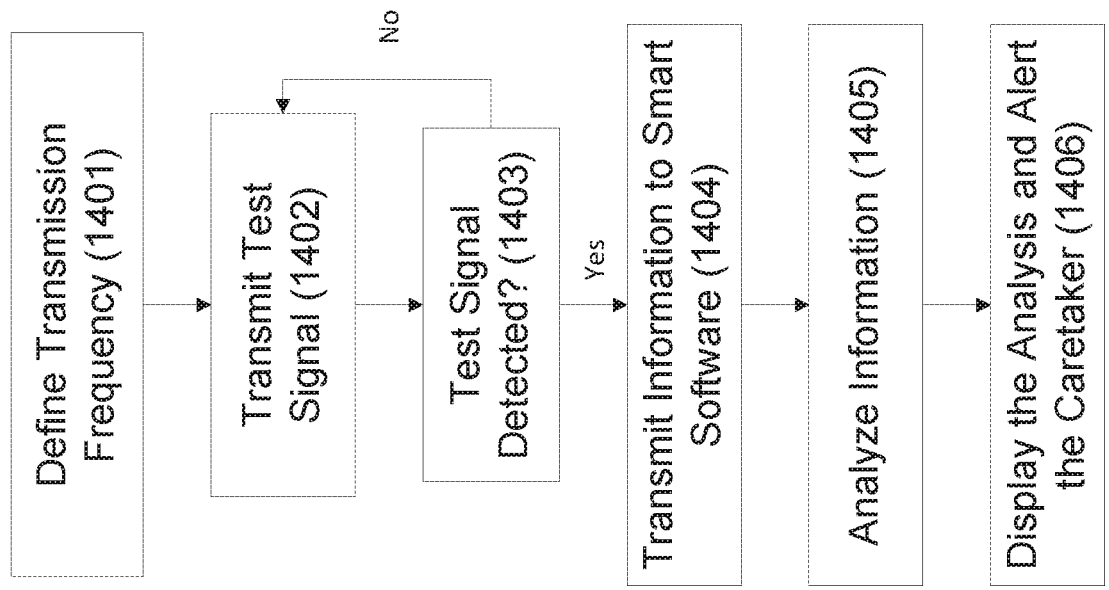
FIG. 14 shows an example flow process for alarming a caretaker when human waste is detected in a smart diaper according to an example embodiment.

FIG. 14 shows an example flow process for alarming a caretaker when human waste is detected in a smart diaper according to an example embodiment. In step 1401, a caretaker defines the frequency of transmission of test signals to the sensor pad. In step 1402, the gadget, using the processing circuitries and through the contacts of its gadget port transmits a test signal. In step 1403, the gadget determines whether it can detect the test signal at a second contact of the gadget port which is connected to an element of the sensor port of the sensor pad. If the test signal is detected, the next step is performed; otherwise, the process returns to step 1402. At step 1404, the gadget transmits this information to the Smart Software of the Smart Device. At step 1405, the Smart Software evaluates the information transmitted from the gadget. For example, the Smart Software determines which zones were short circuited, or determines a conductivity level of the human waste. In step 1406, the Smart Software causes the Smart Device to display the analysis conducted by the Smart Software in the user interface of the Smart Device. Additionally, the Smart Software alerts the caretaker about the presence of the human waste.

In an example embodiment, the gadget software can communicate a temperature measurement inside the smart diaper. The Smart Software is configured to display this information to the user. For example the Smart Software can present a graph indicating the temperature over a period of time. Additionally, the Smart Software can display the instantaneous temperature. In some embodiments, the Smart Software can provide the caretaker with various options for alerting the caretaker about the temperature of the wearer.

In an example embodiment, the caretaker can determine how often the temperature is detected by the gadget. For example, in the user interface of the Smart Software, there can be an option for setting the frequency for detection of the temperature, and upon selecting this option, the caretaker can choose the frequency. As another example, the caretaker can select the frequency using a button provided on the gadget. There can be several modes of detection of the temperature. In an example embodiment, the gadget can detect the temperature continuously. In another example embodiment, the temperature can be detected intermittently. For example, the gadget can wait for a predetermined period of time between two consecutive detections of the temperature. In yet another example embodiment, the gadget can detect the temperature at random times.

Figure 15:
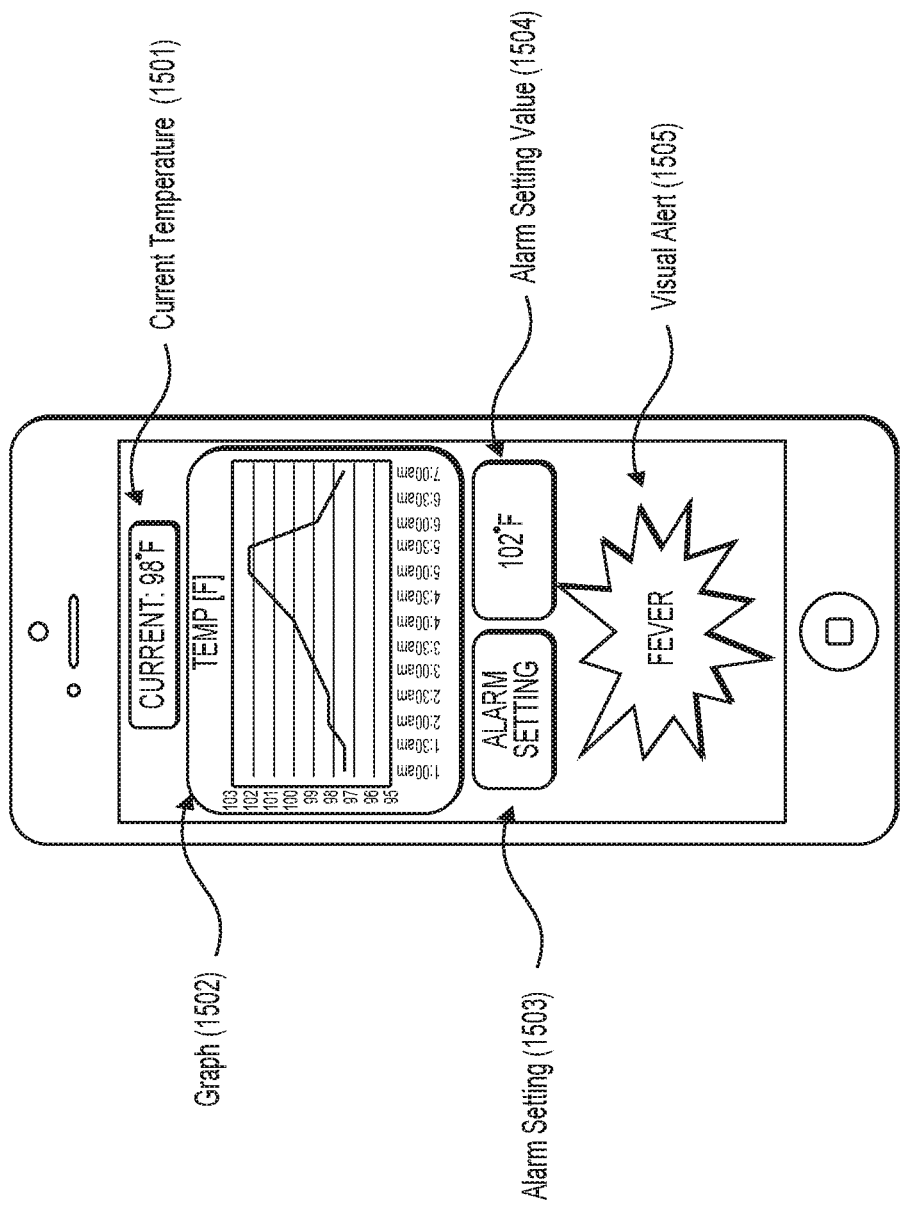
FIG. 15 illustrates an example user interface of a Smart Software according to an example embodiment.

FIG. 15 illustrates an example user interface of a Smart Software according to an example embodiment. In this example embodiment, a temperature inside the smart diaper can be detected and can be communicated to the Smart Software of the Smart Device. The Smart Software is configured to display this temperature in the current temperature field 1501 of the user interface of the Smart Software. Additionally, the Smart Software is configured to retain historical values for the temperature inside the smart diaper and graph this information in the user interface of the Smart Software. For example, the user interface of this example embodiment includes a graph 1502, which displays the temperature over the past few hours. The caretaker can touch the graph, and change the scale of the graph. Moreover, the user interface can provide for an alarm setting field 1503. By touching the alarm setting field 1503, the caretaker can be prompted to set a threshold temperature over which the Smart Software can alert the caretaker. The user interface of the Smart Software is configured to display this value in a field 1504, alarm setting value. When the temperature inside the smart diaper exceeds the threshold value, the Smart Software of the Smart Device is configured to alert the caretaker. This alert can be a visual alert 1505 displayed in FIG. 15. In some embodiments, the caretaker can define a threshold time to be reached before the Smart Software can alert the caretaker that the temperature inside the smart diaper has exceeded the temperature threshold value. This threshold time value can be defined in the user interface of the Smart Software.

Figure 16:
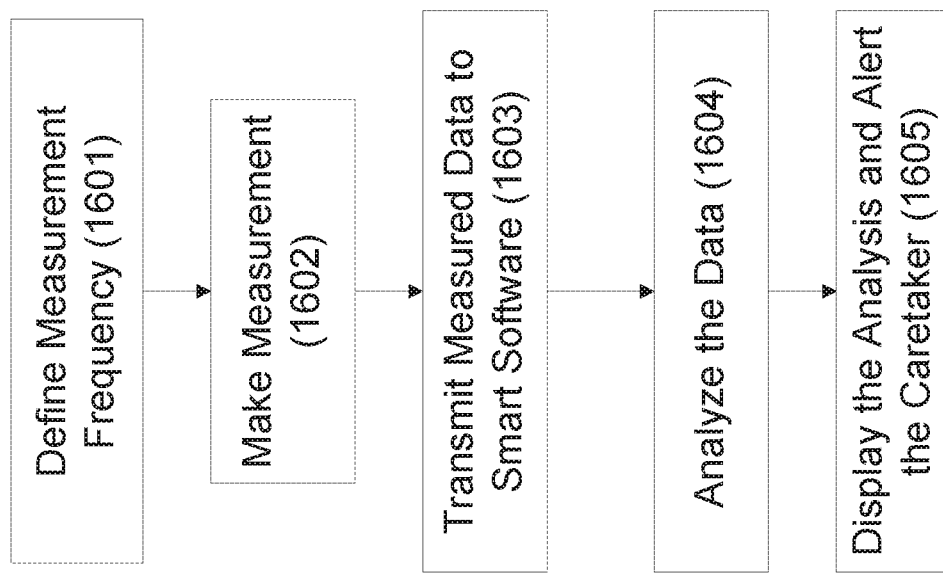
FIG. 16 shows an example flow process for measuring and displaying a temperature inside the smart diaper according to an example embodiment.

FIG. 16 shows an example flow process for measuring and displaying a temperature inside the smart diaper according to an example embodiment. In step 1601, a caretaker defines the frequency of measuring a temperature inside the smart diaper. For example, the gadget can make a measurement every two hours. In step 1602, the gadget, using the processing circuitries and through the contacts of its gadget port measures a resistance of the RTD included on the sensor pad. At step 1603, the gadget transmits the resistance value of the RTD to the Smart Software of the Smart Device. In step 1604, the Smart Software evaluates this information transmitted from the gadget. For example, the Smart Software compares the gadget measurement to a table of reference values, and based on this comparison, determines a current temperature of the inside of the smart diaper. In step 1605, the Smart Software causes the Smart Device to display the analysis conducted by the Smart Software in the user interface of the Smart Device. For example, the Smart Software displays a graph indicating the temperature over the past day for the inside of the smart diaper. Additionally, the Smart Software alerts the caretaker if the temperature has exceeded a predetermined temperature value.

Tracking Functionalities

In an example embodiment, the gadget software can communicate information based on which a location of the smart diaper can be estimated. This location can be relative to a Smart Device or other known structures (e.g., one or more access points). Various technologies can be used in implementing a tracking system. In a first tracking embodiment, the tracking system can use the Bluetooth technology. Various techniques are known for determining the distance of a gadget from another Bluetooth device (or Smart Device). For example, Received Signal Strength Indication ("RSSI") and Time of Flight ("ToF") are two non-exhaustive exemplary techniques in this regard. In the RSSI technique, the intensity of the received signal is measured from the Bluetooth device. Subsequently, a propagation model is used to determine the distance between the gadget and the Bluetooth device. In the ToF technique, a travel time for a signal emitted by the Bluetooth device to the gadget and the return time from the gadget to the Bluetooth device is measured. Using these measurements, the distance between the gadget and the Bluetooth device is determined, In a second tracking embodiment, the tracking system can use a Wi-Fi technology. Various techniques are known for determining the location of a gadget relative to the location of one or more wireless access points (i.e., localization of the gadget relative to the access points). RSSI, Fingerprinting, Angle of Arrival ("AoA") and ToF are four such exemplary techniques. In this tracking embodiment, the Smart Device can be connected to the wireless access points, and can perform any of the named localization techniques to determine the relative location of the gadget.

In the RSSI technique, the intensity of the received signal is measured from several different access points. Subsequently, a propagation model is used to determine the distance between the gadget and each access point. Then, trilateration techniques can be used to calculate the estimated gadget position relative to a known position of the access points. The Fingerprinting technique includes two steps. In the first step, at various locations in the building, a collection of Wi-Fi signals from the access points is sampled to create a position fingerprint. In the second step, which is the online positioning step, fingerprint information is collected around the position to be localized and compared with the sampled position fingerprint. In the AoA technique, multiple antennas are used to estimate an angle of arrival of the multipath signals received at the antenna arrays in the access points. Subsequently, the triangulation technique is used to calculate the location of the gadget. In the ToF technique, a travel time for a signal to the gadget and a return time from the gadget is measured. Using these measurements, the distance between the gadget and the access point is determined, and hence, a trilateration technique can be used to calculate the estimated position of the gadget relative to the access points.

The Smart Software can implement these tracking features of the present disclosures in various implementations. In a first technical implementation, the tracking systems can alert the caretaker when no tracking signals are received from the wearer's smart diaper (i.e., the gadget is outside of a detection range). In this situation, the pairing is severed from the Smart Device or the connection to the Smart Device is lost. In this technical implementation, the Smart Device continuously or intermittently can check its paring or connection with the gadget of the diaper to determine whether the connection still exists. A caretaker can define how often the pairing or connection is checked. If the connection exists, the Smart Device continues its operation. However, if the Smart Device determines that the connection has been lost, the Smart Device determines whether it should alert the caretaker. The caretaker can set a threshold time period for the Smart Device to wait before alerting the caretaker. Setting a threshold time period is optional. If during this time period the pairing or connection is restored, the Smart Device does not alert the caretaker. However, if the connection is still not restored, the Smart Device alerts the caretaker. The alert can be in the form of showing an image or video on, or vibration of the Smart Device, or a combination thereof.

In the second technical implementation, the Smart Device alerts the caretaker based on the distance of the smart diaper from the Smart Device (or from a predetermined area). In this technical implementation, the Smart Device can determine the distance of the smart diaper from the Smart Device or a predetermined area. The caretaker can set a predetermined separation distance between the smart diaper and the Smart Device over which the caretaker wants to be alerted by the Smart Device. The smart diaper is considered to be disconnected from the Smart Device when the distance between the smart diaper and the Smart Device increases to a distance over the predetermined distance. Similar to the previous technical implementation, the Smart Device continuously or intermittently scans the connection between the Smart Device and the smart diaper. Once the smart diaper is disconnected from the Smart Device (i.e., the separation distance increases to a distance over the predetermined distance), the Smart Device determines whether to alert the caretaker. In some embodiments, the caretaker can define a threshold time period that has to pass before the Smart Device alerts the caretaker. Once the Smart Device determines that the smart diaper is disconnected from the Smart Device, if the smart diaper comes back into the range before the threshold time period expires, the Smart Device does not alert the caretaker. However, if the smart diaper remains disconnected after the threshold time period has exceeded, the Smart Device alerts the caretaker as described above.

Figure 17:
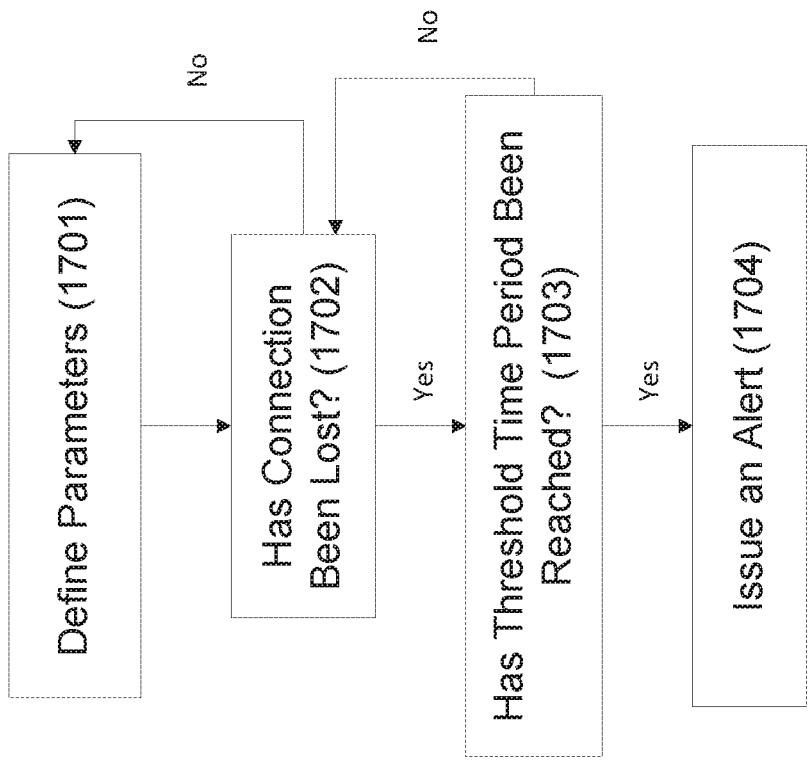
FIG. 17 shows a flow process for notifying a caretaker via the Smart Device when the wearer leaves a predefined perimeter.
Figure 18:
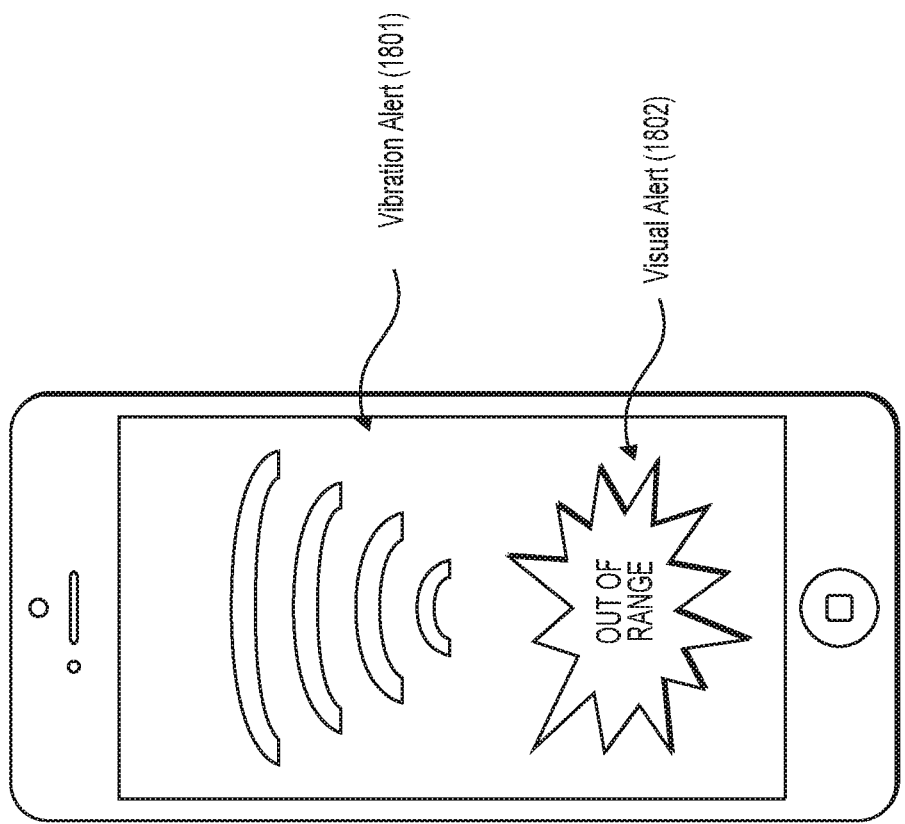
FIG. 18 illustrates an example user interface of a Smart Software which can be alerting a caretaker when the smart diaper connected or paired to the Smart Software is out of the predefined perimeter.

FIG. 17 shows a flow process for notifying a caretaker via the Smart Device when the wearer leaves a predefined perimeter. In step 1701, the caretaker defines a set of parameters for alerting the caretaker when the wearer leaves the predefined perimeter. For example, the caretaker can define how often the Smart Software monitors the connection between the gadget and the Smart Device, or the caretaker can define the threshold time period after which the Smart Device can alert the caretaker about the lack of connectivity between the gadget and the Smart Device. These parameters can be defined at the Smart Software or at the gadget software. In instances in which these parameters are defined at the Smart Software, the Smart Software can communicate these parameters to the gadget software. In step 1702, the Smart Software continuously or intermittently detects the connection between the gadget and the Smart Device, and the Smart Software determines whether the connection has been lost. If the connection has been lost, in step 1703, the Smart Software determines whether the connection has been lost for longer than the threshold time period. If the connection has been lost for longer than the threshold time period, then at step 1704, the Smart Device alerts the caretaker. FIG. 18 illustrates an example user interface of a Smart Software which can be alerting a caretaker when the smart diaper connected or paired to the Smart Software is out of the predefined perimeter. In this example embodiment, the Smart Device alerts the user by displaying a visual alert 1802 and a vibration alert 1801 at the same time.

Figure 19:
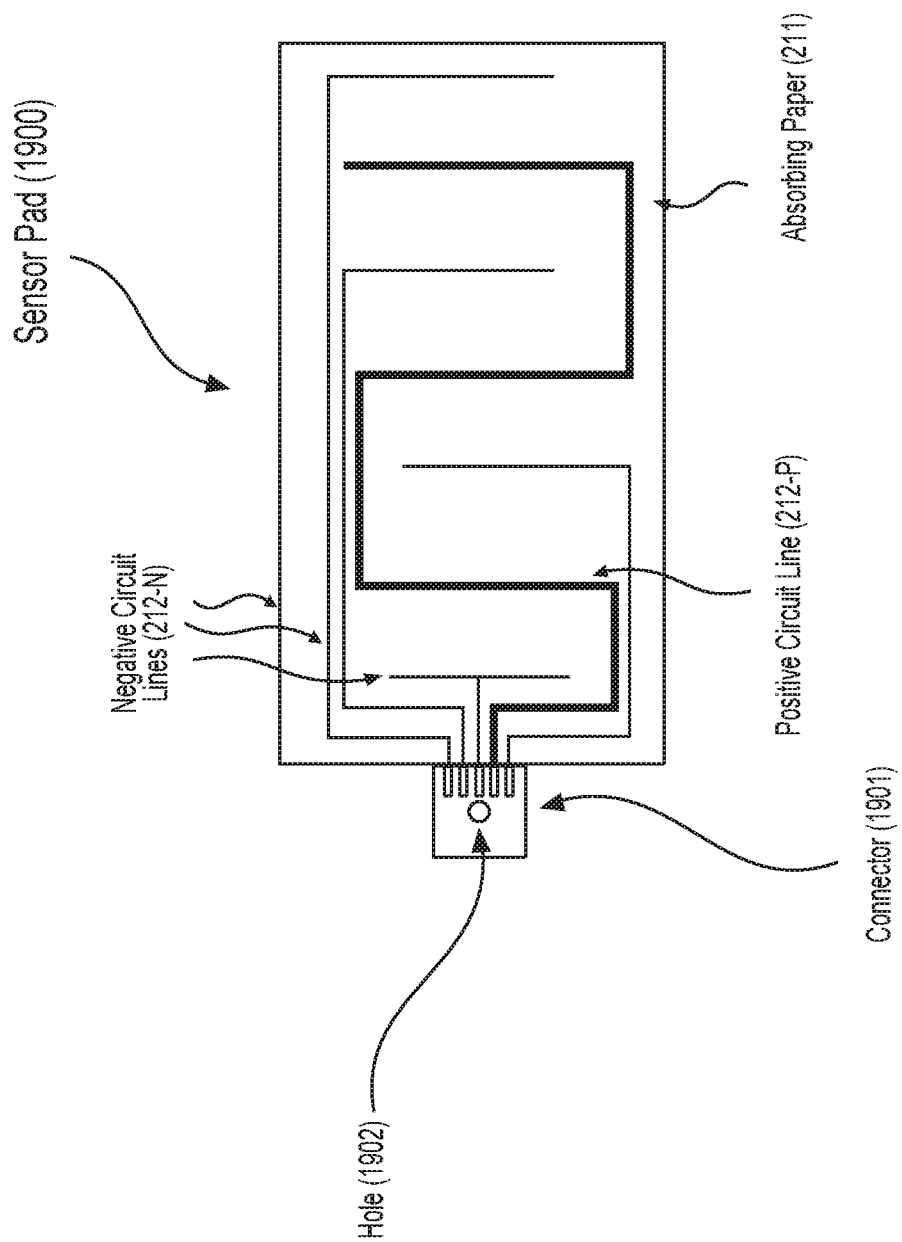
FIG. 19 illustrates yet another example embodiment of a sensor pad including a connector.

FIG. 19 illustrates yet another example embodiment of a sensor pad including a connector. In this example embodiment, the absorbing paper 211 of the sensor pad 1900 can be cut in a way that a connector 1901 is provided on the absorbing paper 211. The connector 1901 can include a hole 1902, which can secure the connector 1901 to a gadget. Printing the connector 1901 on the absorbing paper 211 of the sensor pad 1900 can obviate the need for a separate connector and can facilitate the manufacturing process.

Figure 20:
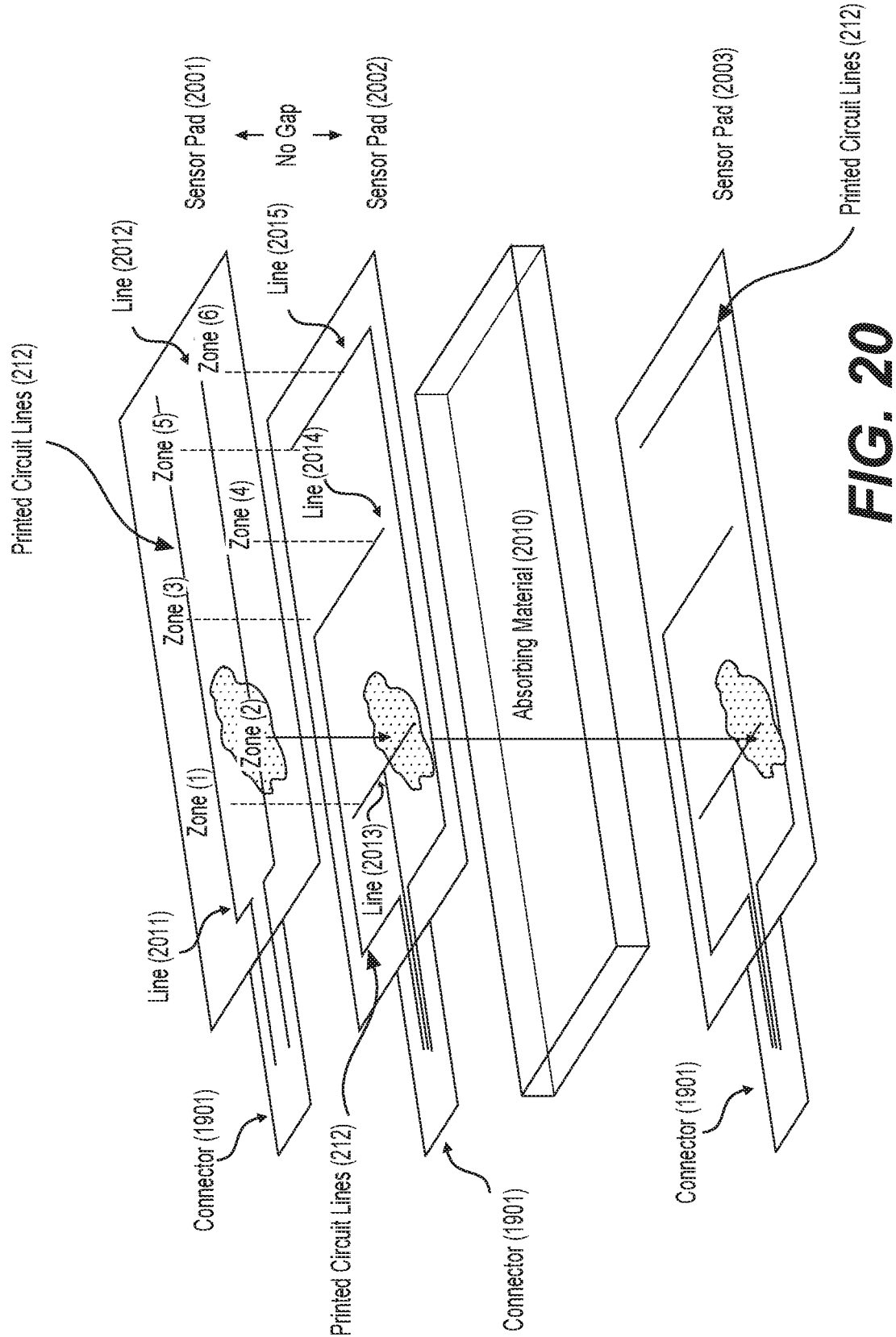
FIG. 20 illustrates an example embodiment of several sensor pads arranged in an absorbent core of a smart diaper.

FIG. 20 illustrates an example embodiment of several sensor pads arranged in an absorbent core of a smart diaper. As described before, sensor pads can be printed so that they can be folded and create a three-dimensional sensor. Alternatively (or in addition to foldable sensor pads), in an example embodiment, several sensor pads can be provided so that the combination of the sensor pads can detect moisture in a three-dimensional space. In this example embodiment, three sensor pads 2001, 2002, and 2003 are provided. The absorbing material 2010 can be located in between sensor pads 2001, 2002, and 2003.

Each sensor pad can include at least one printed circuit line 212. In an example embodiment, moisture detection can be provided for each individual sensor pad, e.g., the gadget can transmit a signal to one of the printed circuit lines 212 of a sensor pad and detect the transmitted signal at another printed circuit line 212 of the sensor pad. Alternatively (or in addition to detection within a sensor pad), the moisture detection can take place between multiple sensor pads. For example, the gadget can transmit a signal to the printed circuit lines 212 of the sensor pad 2001 and detect the transmitted signal at the printed circuit lines 212 of the sensor pad 2002. As such, if there is a wet region formed between the sensor pads 2001 and 2002, the printed circuit lines 212 on the sensor pad 2001 and 2002 can be short circuited and thereby inform the caretaker about the presence of moisture in the region. Similarly, the gadget can transmit or detect signals through the sensor pad 2003, and receive information regarding the wetness of the space between the sensor pad 2003 and the sensor pads 2001 or 2002.

In an example embedment, the identity of the line through which a signal is transmitted and the line through which the signal is detected determines a detection zone for the gadget. Using the identity of the detection zone exposed to moisture, the caretaker can be informed about the volume of human waste present in the smart diaper as well as the type of the waste. In the example embodiment of FIG. 20, the sensor pad 2001 can include the circuit lines 2011 and 2012. The sensor pad 2002 can include the circuit lines 2013, 2014, and 2015. A short circuit between the line 2011 and the line 2013 can inform the gadget that detection zone 1 is exposed to moisture. A short circuit between the line 2012 and the line 2013 can inform the gadget that the detection zone 2 is exposed to moisture. A short circuit between the line 2011 and the line 2014 can inform the gadget that the detection zone 3 is exposed to moisture. A short circuit between the line 2012 and the line 2014 can inform the gadget that the detection zone 4 is exposed to moisture. A short circuit between the line 2011 and the line 2015 can inform the gadget that the detection zone 5 is exposed to moisture. A short circuit between the line 2012 and the line 2015 can inform the gadget that the detection zone 6 is exposed to moisture.

Figure 21:
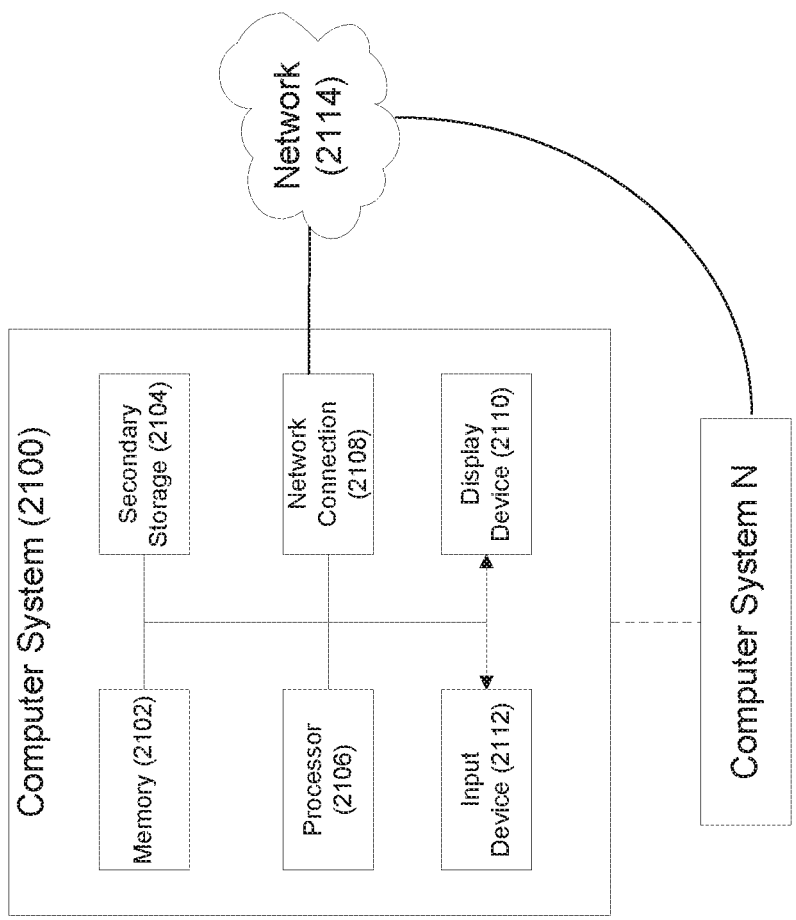
FIG. 21 illustrates exemplary hardware components for implementing embodiments of a system and apparatus for a smart diaper.

FIG. 21 illustrates exemplary hardware components for implementing embodiments of a system and apparatus for a smart diaper. A computer system 2100, or other computer systems similarly configured, may include and execute one or more subsystem components to perform functions described herein, including the steps of various flow processes described above. Likewise, a mobile device, a cell phone, a smartphone, a laptop, a desktop, a notebook, a tablet, a wearable device, a server, etc., which includes some of the same components of the computer system 2100, may run an application (or software) and perform the steps and functionalities described above. Computer system 2100 may connect to a network 2114, e.g., Internet, or other network, to receive inquires, obtain data, and transmit information and incentives as described above.

The computer system 2100 typically includes a memory 2102, a secondary storage device 2104, and a processor 2106. The computer system 2100 may also include a plurality of processors 2106 and be configured as a plurality of, e.g., bladed servers, or other known server configurations. The computer system 2100 may also include a network connection device 2108, a display device 2110, and an input device 2112.

The memory 2102 may include RAM or similar types of memory, and it may store one or more applications for execution by processor 2106. Secondary storage device 2104 may include a hard disk drive, floppy disk drive, CD-ROM drive, or other types of non-volatile data storage. Processor 2106 executes the application(s), such as those described herein, which are stored in memory 2102 or secondary storage 2104, or received from the Internet or other network 2114. The processing by processor 2106 may be implemented in software, such as software modules, for execution by computers or other machines. These applications preferably include instructions executable to perform the system and subsystem component functions and methods described above and illustrated in the FIGS. herein. The applications preferably provide graphical user interfaces (GUIs) through which users may view and interact with subsystem components (or the Smart Software in the Smart Device).

The computer system 2100 may store one or more database structures in the secondary storage 2104, for example, for storing and maintaining the information necessary to perform the above-described functions. Alternatively, such information may be in storage devices separate from these components.

Also, as noted, processor 2106 may execute one or more software applications in order to provide the functions described in this specification, specifically to execute and perform the steps and functions in the process flows described above. Such processes may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the computer system 2100 (or the Smart Software of the Smart Device).

The input device 2112 may include any device for entering information into the computer system 2100, such as a touch-screen, keyboard, mouse, cursor-control device, touch-screen, microphone, digital camera, video recorder or camcorder. The input and output device 2108 may be used to enter information into GUIs during performance of the methods described above. The display device 2110 may include any type of device for presenting visual information such as, for example, a computer monitor or flat-screen display (or mobile device screen). The display device 2110 may display the GUIs and/or output from sub-system components (or software).

Examples of the computer system 2100 include dedicated server computers, such as bladed servers, personal computers, laptop computers, notebook computers, palm top computers, network computers, mobile devices, or any processor-controlled device capable of executing a web browser or other type of application for interacting with the system.

Although only one computer system 2100 is shown in detail, system 2100 may use multiple computer system or servers as necessary or desired to support the users and may also use back-up or redundant servers to prevent network downtime in the event of a failure of a particular server. In addition, although computer system 2100 is depicted with various components, one skilled in the art will appreciate that the system can contain additional or different components. In addition, although aspects of an implementation consistent with the above are described as being stored in a memory, one skilled in the art will appreciate that these aspects can also be stored on or read from other types of computer program products or computer-readable media, such as secondary storage devices, including hard disks, floppy disks, or CD-ROM; or other forms of RAM or ROM. The computer-readable media may include instructions for controlling the computer system 2100, to perform a particular method, such as methods described above.

The terms and descriptions used herein are set forth by way of illustration only and are not meant as limitations. Those skilled in the art will recognize that many variations are possible within the spirit and scope of these disclosures as defined in the following claims, and their equivalents, in which all terms are to be understood in their broadest possible sense unless otherwise indicated.

The invention claimed is:

1. A diaper comprising:
a main panel having an interior surface in contact with skin of a user during use and an exterior surface exposed to an environment surrounding the user;
a sensor pad integral to the main panel of the diaper and defining at least two detection zones associated with the interior surface of the main panel;
a sensor port positioned on and accessible via the exterior surface of the main panel, the sensor port electrically coupled to the sensor pad through the main panel; and
a gadget including a gadget port for releasably coupling the gadget to the sensor port, such that the gadget is entirely maintained on an exterior of the diaper during use and wherein
the gadget is electrically connected to the sensor pad via the sensor port;
the gadget send a test signal to the sensor pad via the sensor port and determines, based at least in part on a detected response to the test signal, that the gadget is properly connected to the sensor port; and
the gadget is configured to detect an exposure of the sensor pad to human waste at one or more of the at least two detection zones, and responsive to the exposure, transmit an alert signal to a remote smart device, the alert signal indicating a location of the human waste via an identification of the detection zone of the at least two detection zones in which the exposure was detected.

2. The diaper of claim 1, wherein each detection zone of the at least two detection zones is assigned one or more distinct circuit lines.

3. The diaper of claim 1, wherein the gadget includes a battery, processing circuitries, and a transceiver.

4. The diaper of claim 3, wherein the transceiver is configured to be connected to the smart device.

5. The diaper of claim 1, wherein the sensor port includes two or more holes, each of the two or more holes configured to fasten with a pin of the gadget, each of the two or more holes to align during use.

6. The diaper of claim 1, further comprising:
two or more tracking antennas position along the main panel, each of the tracking antennas to estimate an angle of arrival of a signal from an access point; and
wherein a distance of the gadget relative to the access point is determined based at least in part on the angle of arrival of the signal at each of the two or more tracking antennas; and
wherein an alert signal is transmitted via the access point in response to the distance meeting or exceeding a user determined separation distance.

7. The diaper of claim 6, wherein the two or more tracking antennas are positioned on a first portion of the main panel and the sensor port is positioned on a second portion of the main panel, the first portion located along a back of a user during use and the second portion located along a front of the user during use.

8. A system comprising:
a diaper, including:
a main panel having an interior surface exposed to skin of a user during use and an exterior surface exposed to an environment surrounding the user during use;
a sensor pad defining a plurality of detection zones associated with the interior surface of the main panel;
a sensor port positioned on and accessible via the exterior surface of the main panel, the sensor port electrically coupled to the sensor pad through the main panel; and
a gadget releasably coupled to sensor port of the sensor pad via the exterior surface of the main panel, the gadget maintained entirely on an exterior of the diaper during use; and a smart device in wireless communication with the gadget;

wherein the gadget is electrically connected to the sensor pad via the sensor port;

the gadget send a test signal to the sensor pad via the sensor port and determines, based at least in part on a detected response to the test signal, that the gadget is properly connected to the sensor port; and the gadget is configured to detect an exposure of the sensor pad to human waste, and responsive to the exposure, transmit an alert signal to the smart device, the alert signal including an indication of a location of the human waste via an identification of a first detection zone of the plurality of detection zones associated with the exposure.

9. The system of claim 8, wherein the smart device includes an application which is configured to notify a user of the smart device.

10. The system of claim 9, wherein responsive to receiving the alert signal, the application is configured to notify the user.

11. The system of claim 10, wherein the application is configured to receive a user input indicating a period of time, and the application is further configured to retain the alert signals for the period of time, and display the total number of signals over the period of time to the user.

12. The system of claim 8, wherein the sensor pad includes a resistance temperature detector.

13. The system of claim 12, wherein the gadget is configured to transmit a temperature signal to the smart device, the temperature signal being a resistance of the resistance temperature detector.

14. The system of claim 13, wherein the smart device includes an application which is configured to determine a temperature value based on the temperature signal transmitted by the transceiver and to notify a user of the smart device of the temperature value.

15. The system of claim 8, wherein the diaper includes at least one antenna.

16. The system of claim 15, wherein the smart device is configured to determine a distance between the transceiver and the smart device.

17. The system of claim 16, wherein the smart device uses a received signal strength indication technique for determining the distance between the transceiver and the smart device.

18. A gadget comprising:

a gadget port to releasably coupled the gadget to a sensor port of a sensor pad of a main panel of a diaper and to maintain an entirety of the gadget exterior to the diaper, wherein the sensor port is positioned along an exterior surface of the main panel, the sensor pad is positioned along an interior surface of the main panel, and the sensor port is electrically coupled to the sensor pad through at least a portion of the main panel;

a circuitry component to detect an exposure of the sensor pad to human waste; and responsive to the exposure, a wireless communication interface to transmit an alert signal to a smart device in wireless communication with the gadget, the alert signal including an indication of a location of the human waste via an identification of a first detection zone of the plurality of detection zones of the sensor pad associated with the exposure;

wherein the gadget sends a test signal to the sensor pad via the sensor port and determines, based at least in part on a detected response to the test signal, that the gadget is properly connected to the sensor port.

19. The gadget of claim 18, wherein the alert signal includes an indication of a time associated with the exposure.

* * * * *